United States Patent [19]

Kit et al.

[11] Patent Number: 4,999,296

[45] Date of Patent: * Mar. 12, 1991

[54] THYMIDINE KINASE NEGATIVE INSERTION MUTANTS OF PSEUDORABIES VIRUS AND METHODS FOR THE PRODUCTION OF SAME

[75] Inventors: Malon Kit; Saul Kit, both of Houston, Tex.

[73] Assignees: NovaGene, Inc.; Baylor College of Medicine, both of Houston, Tex.

[*] Notice: The portion of the term of this patent subsequent to Apr. 30, 2002 has been disclaimed.

[21] Appl. No.: 857,703

[22] Filed: Apr. 29, 1986

[51] Int. Cl.$^5$ .................... C12P 21/00; C12N 15/00; C12N 7/00

[52] U.S. Cl. .................. 435/235.1; 435/172.1; 435/172.3; 435/320.1; 435/69.1; 435/70.1; 435/70.3; 935/22; 935/23; 935/32; 935/52; 935/57; 935/65; 935/63

[58] Field of Search ............. 435/68, 70, 91, 235, 435/317, 69.1, 70.1, 172.3; 836/22; 424/89, 85; 935/32, 37, 57, 65

[56] References Cited

U.S. PATENT DOCUMENTS

| | | | |
|---|---|---|---|
| 4,609,548 | 9/1986 | Kit et al. | 424/89 |
| 4,680,176 | 7/1987 | Berns et al. | 424/89 |
| 4,711,850 | 12/1987 | Kit et al. | 435/235 |
| 4,753,884 | 1/1988 | Kit et al. | 435/235 |
| 4,769,331 | 9/1988 | Roizman et al. | 435/172.3 |

FOREIGN PATENT DOCUMENTS 0074808 3/1983 European Pat. Off. .
0162738 11/1985 European Pat. Off. .

OTHER PUBLICATIONS

Mettenleiter et al., (1985), J. Virology 56: 307–311.

Primary Examiner—Richard A. Schwartz
Assistant Examiner—Anne Brown
Attorney, Agent, or Firm—Sughrue, Mion, Zinn, Macpeak & Seas

[57] ABSTRACT

The present invention relates to pseudorabies viruses which fail to produce any functional thymidine kinase as a result of an insertion in the thymidine kinase gene, vaccines against pseudorabies containing the same, and methods for the production and use of the same. The present invention also relates to pseudorabies virus based viral vectors for the coexpression of foreign genes.

14 Claims, 5 Drawing Sheets

THYMIDINE KINASE NEGATIVE INSERTION MUTANTS OF PSEUDORABIES VIRUS AND METHODS FOR THE PRODUCTION OF SAME

The invention described herein was developed during the tenure of a Research Career Award to Saul Kit from the United States Public Health Service of the Department of Health and Human Services.

FIELD OF INVENTION

The present invention relates to pseudorabies viruses which fail to produce any functional thymidine kinase as a result of an insertion in the thymidine kinase gene, vaccines against pseudorabies containing the same, and methods for the production and use of the same. The present invention also relates to pseudorabies virus based viral vectors useful for the coexpression of foreign genes.

BACKGROUND OF INVENTION

I. Pseudorabies Disease

Pseudorabies, a highly contagious disease of swine and other livestock, such as cattle sheep and goats, is caused by *Herpesvirus suis* (hereinafter "pseudorabies virus" or "PRV"). In swine, the disease causes respiratory illness and encephalitis which may progress to death. Other common consequences of infection in swine are abortions neonatal demise, reduced litter size and slower growth rates. In other livestock, most notably cattle, PRV infection almost invariably proceeds to a lethal encephalitis.

Pseudorabies has become a major threat and cause of economic loss to the swine industry throughout the world. There is also considerable alarm over the spread of pseudorabies to cattle and other farm animals. Within the last ten years, economic losses have escalated because of the emergence of more virulent strains of PRV and the widespread dissemination of the disease. Today, it is estimated that 8.0% of the 80 million hogs on farms in the United States are infected in comparison to less than 0.8% a decade ago.

The clinical symptoms and consequences of PRV infection may be moderated or prevented by the use of vaccines comprising either killed or modified live, i.e., attenuated strains of PRV. However, most existing vaccines have failed to control the spread of pseudorabies disease because of a unique biological property of PRV and the other alpha-herpesviruses, such as herpes simplex virus types 1 and 2, varicella-zoster, infectious bovine rhinotracheitis virus, marmoset herpesvirus, and equine herpesvirus type 1.

More specifically, alpha-herpesviruses have the special ability to enter into a dormant state in neural tissues. That is, as an animal recovers from the initial generalized infection alpha-herpesviruses retreat to portions of the nervous system where they become quiescent and impervious to the body's immune defenses. This dormant infection, i.e., latency, may be unexpectedly reactivated, resulting in recrudescence of disease or in a contagious condition known as the carrier state, wherein the infected animal shows no outward symptoms of the disease but can transmit or "shed" infectious alpha-herpesviruses intermittently so as to cause the spread of infection and epidemic outbreaks.

II. Known Modified Live Virus PRV Vaccines

Previously, modified live virus PRV vaccines have been produced by multiple passages of the virus 1in chick and/or monkey tissue culture cells (see: Skoda, R., Brauner, I., Sadecky, E., and Mayer V. *Acta Virol.* 8:1-9 (1964) and Bartha A. *Magy. Allatorv. Lapja* 16:42-45 (1961)). During tissue culture passages, mutations accumulate as the virus adapts to its new environment. These undefined mutations adversely affect virus reproduction in the natural host, resulting in virus attenuation.

A problem with the above-described modified live virus PRV vaccines is that the animal often becomes a carrier of the dormant vaccine virus. As a result, usage of these vaccines can result in two undesirable situations which impede their safety and effectiveness. First, abortions, stillbirths and fatal infections in newborns can be caused by some vaccine viruses as they are shed by vaccinated carriers. Second, the repeated circulation of vaccine virus within a herd can result in a reversal of the process of attenuation such that the vaccine virus reverts to the pathogenic parent strain. Under such circumstances, widespread vaccination will undesirably promote the dissemination of the disease.

In addition to the above-described disadvantages, the previously known PRV vaccines while substantially minimizing symptoms of illness, do not prevent the animal from acquiring a dormant infection with pathogenic field strains. Thus, despite vaccination an animal may become a carrier of the disease and transmit it to susceptible animals. These carriers of the disease, when moved between farms and market, will shed not only the dormant vaccine virus as discussed above, but also the disease virus. This results in the undesirable transmission of the disease across geographic barriers and state boundaries.

In order to overcome the above-described disadvantages, temperature-resistant pseudorabies viruses which fail to produce any functional thymidine kinase (hereinafter "TK") enzyme as a result of either a mutagen-induced mutation or a deletion in the thymidine kinase gene (hereinafter "tk gene") have been developed (see: U.S. Pat. No. 4,514,497, which U.S. patent is incorporated by reference herein in its entirety). These mutants have been shown to be safe and efficacious in the prevention of pseudorabies disease when used as vaccines. (see: Kit, S., Kit. M., and Pirtle, E. C. *Am. J. Vet. Res.* 46:1359-1367 (1985) and Kit S., Kit. M., Lawhorn, B., and McConnell, S., In: *High-Technology Route to Virus Vaccines* Eds. Dreesman, G. R., Bronson, J. G., and Kennedy R. C. (American Society of Microbiology, Washington, D.C.), pp. 82-99 (1985)).

As an alternative to the above-described deletion mutant of PRV, the present invention was developed. Specifically, the present invention relates to pseudorabies virus mutants that fail to produce any functional thymidine kinase as a result of an insertion in the tk gene. Based on the findings that the above-described deletion mutants are safe and efficacious vaccines against pseudorabies disease, it is believed that the insertion mutants of the present invention will also be useful as vaccines against pseudorabies disease. The development of this embodiment of the present invention is based in part on the description of the location of the PRV tk gene, the nucleotide sequence thereof and the enrichment and selection procedures developed for isolating the PRV thymidine kinase negative mutants described in U.S. Pat. No. 4,514,497. That is, prior to U.S. Pat. No. 4,514,497, it had not been possible to develop pseudorabies virus mutants that fail to produce any functional thymidine kinase as a result of an insertion in the tk gene because it was not known in the art (1) the approximate boundaries of the nucleotide sequences delineating the coding region of the PRV tk gene: (2) the restriction nuclease sites within the PRV tk gene to allow appropriate insertions to be made in a cloned PRV tk gene: and (3) what selection drugs could be employed i.e.. the drugs which can be employed with other alpha-herpesviruses are inadequate for PRV and thus it was necessary to develop modified enrichment and selection procedures therein. As a result, prior to U.S. Pat. No. 4,514,497, there was insufficient information to engineer and isolate an insertion mutant in the PRV tk gene since the known procedures would not work in the PRV system.

III. Viral Based Vectors

During the last few years, recombinant DNA technology has permitted the construction of chimeric viruses which express genetic information from more than one origin. A variety of unique virus based vectors have been developed such as adenovirus based vectors (see: Ruether, J. E., Maderious, A., Lavery, D., Logan, J., Fu, S. M., Chen-Kiang, S., *Mol. and Cell. Biol.* 6:123–133 (1986); and Haj-Ahmad, Y. and Graham, F. L., *J. Virol.* 57:267–274 (1986)) as well as herpes simplex virus based vectors (see: Smith. M., Arsenakis, M., Tiollais, P., and Roizman, B., *Proc. Natl. Acad. Sci.*, USA 81:5867–5870 (1984)) and Herpes Saimiri virus based vectors (see: Desrosiers, Kamine, J., Bakker, A , Silve, D., Woychik, R. B., Sakai, D. D., and Rottman, F. M., *Mol. and Cell. Biol.* 5:2796–2803 (1985)).

The most extensively developed and exploited virus based vectors are the vaccinia virus based vectors (see: Mackett, M., Smith, G. L., and Moss, B., *Proc. Natl. Acad. Sci.*, USA 79:7415–7419 (1982); Panicali, D. and Paoletti, E., *Proc. Natl. Acad. Sci.*, *USA* 79:4927–4931 (1982)). Vaccinia virus based vectors which have been described include those which are useful as vaccines for hepatitis B (see: Smith, G. L., Mackett, M. and Moss, B., Nature 302:490–492 (1983): rabies (see: Kieny, M. P. et al. *Nature* 312:163–166 (1984) and Wiktor, T. F., MacFarland, R. I., Reagan, K. J., Dietzschold, B., Curtis, P. J., Wunner, W. H., Kieny, M. P., Lathe, R., Lecocq, J. P., Mackett, M., Moss, B. and Koprowski, H. K., *Proc. Natl. Acad. Sci.*, USA 81:7194–7198 (1984)); malaria (see: Smith, G. L. et al. *Science* 224:397–399 (1984); influenza (see: Smith, G. L., Murphy, B. R., Moss, B., *Proc. Natl. Acad. Sci.*, USA 80:7155–7159 (1983)); herpes simplex virus (see: Paoletti, E., Lipinskas, B. R., Samsonoff, C., Mercer, S., Panicali, D., *Proc. Natl. Acad. Sci.*, USA 81:193–197 (1984) and Gillespie, J. M., Geissinger, C., Scott, F. W., Higgins, W. P., Holmes, D. F., Perkus, M., Mercer, S. and Paoletti, E., *J. Clin. Microbiol* 23:283–288 (1986)); and vesicular stomatitis virus (see; Mackett, M., Yilma, T., Rose, J. K., Moss, B., *Science* 227:433–435 (1985)). A vaccinia based viral vector which expresses the coding gene sequences of the PRV g92 gene has also been described (see: Robbins, A. K., Watson, R. J., Enquist, L. W., European Patent Publication 0 162 738).

Viral based vectors offer several significant advantages. First, immunization against more than one disease is possible with a single virus strain. This creates economy of production. Secondly, for many vaccines, two or more different modified live viruses can not be employed in combination in a single formulation because the replication of the viruses in the host causes mutual interference, and thereby impairs immunization. This situation is circumvented with the viral based vector because there is only a single replicating genome. Third, vaccines against causative agents of infectious disease, such as viruses and bacteria, for which vaccines have not previously been available or feasible, may for the first time be developed using viral based vectors which express the antigens of the causative agents of infectious disease. This is because the only component of the causative agents of infectious disease which is carried by the viral based vector is the gene coding for the antigen of the causative agent of disease which is responsible for eliciting immunity. Other components of the causative agents of infectious disease that are responsible for the pathobiology of the disease are eliminated from the viral based vector.

The vaccinia based viral vectors are disadvantageous because (1) they infect humans and therefor can pose a health hazard to the public, (2) there is no purpose served in vaccinating animals against small pox, i.e., the disease that vaccinia protects against, and (3) potential recombination events between vaccinia and indigenous animal pox viruses might regenerate virulence of the vaccinia virus which will cause small pox disease in humans.

Pseudorabies based viral vectors are advantageous over vaccinia based viral vectors for vaccination of swine because (1) they protect swine against pseudorabies disease and (2) they are host limiting, i.e., do not infect humans.

The vaccinia based viral vector described in European Patent Publication 0 162 738 is entirely different from the present invention in that (1) it is not a pseudorabies virus based viral vector and thus does not possess the advantageous characteristics thereof and (2) it requires activation of the foreign gene insert, i.e., the PRV g92 gene, by a vaccinia gene promoter rather, than a PRV promoter, e.g., the PRV g92 gene promoter.

Prior to the present invention, it was not possible to produce a pseudorabies based viral vector because there was no knowledge of suitable PRV gene promoters which could be employed therein. In the present invention, the identification and isolation of a PRV DNA fragment containing a PRV gene promoter has for the first time been described. Thus, for the first time in the present invention it has been possible to develop pseudorabies virus based viral vectors.

SUMMARY OF THE INVENTION

An object of the present invention is to provide a pseudorabies vaccine effective in controlling the spread of pseudorabies disease.

Another object of the present invention is to provide a pseudorabies vaccine wherein the animal vaccinated with such is less likely to become a carrier of either the vaccine virus or a field virus.

A further object of the present invention is to provide a pseudorabies virus which cannot revert to tk+ and is easily distinguished from tk+ pseudorabies virus.

An even further object of the present invention is to provide a pseudorabies virus which can replicate efficiently at temperatures ranging from 30° C. to 40° C. i.e.. inclusive of temperature-resistant viruses.

Another object of the present invention is to provide methods for the production of a pseudorabies virus which contain an insertion mutation in the tk gene.

Still another object of the present invention is to provide pseudorabies virus based viral vectors and a method for the production thereof.

Other objects of the present invention will be apparent from the detailed description of the invention hereinafter.

In one embodiment of the present invention the above-described objects have been met by a PRV which fails to produce any functional thymidine kinase as a result of an insertion in the tk gene, and a vaccine for pseudorabies disease comprising:

(1) a pharmaceutically acceptable amount of said virus: and (2) a pharmaceutically acceptable carrier or diluent.

In a further embodiment of the present invention, the PRV also fails to produce any glycoprotein gI as a result of a mutation in the gI gene.

In another embodiment of the present invention, the PRV is a temperature-resistant virus.

In still another embodiment of the present invention, the above-described objects have been met by a process for producing a PRV which fails to produce any functional thymidine kinase as a result of an insertion in the tk gene comprising:

(1) Constructing a hybrid plasmid comprising a cloning vector and a DNA fragment of PRV containing substantially all of the PRV tk gene and flanking sequences thereof;

(2) Inserting a foreign DNA sequence within the coding region of the PRV tk gene of the hybrid plasmid of step (1):

(3) Co-transfecting, in PRV host cells, the hybrid plasmid of step (2) with infectious DNA from a tk+ pseudorabies virus:

(4) Selecting, in tk− PRV host cells, for tk− PRV from the virus produced in step (3) so as to produce a PRV mutant which fails to produce any functional thymidine kinase as a result of an insertion in the tk gene.

In a preferred embodiment, prior to or during step (2), a functional PRV gene promoter is inserted into the PRV tk gene of the hybrid plasmid of step (1) and, in step (2), a foreign gene is inserted adjacent to said PRV gene promoter such that the expression of said foreign gene is controlled by said PRV gene promoter and such that the resulting PRV mutant of step (4) expresses said foreign gene. In this embodiment, prior to step (4) or after step (4), there is an additional step comprising screening for PRV which expresses said foreign gene so as to produce a PRV mutant which fails to produce any functional thymidine kinase as a result of an insertion in the tk gene and expresses said foreign gene.

In an additional embodiment of the present invention, the above-described objects have been met by a pseudorabies virus based viral vector comprising pseudorabies virus having inserted therein a foreign gene adjacent to a PRV gene promoter such that the expression of said foreign gene is controlled by said PRV gene promoter.

In another embodiment of the present invention the above-described objects have been met by a pseudorabies virus based viral vector produced by the process comprising:

(1) Constructing a hybrid plasmid comprising a cloning vector and a DNA fragment of PRV containing substantially all of a non-essential PRV DNA sequence and flanking sequences thereof:

(2) Inserting a PRV gene promoter and a foreign gene adjacent to said PRV gene promoter within the non-essential PRV DNA sequence of the hybrid plasmid of step (1) such that the expression of said foreign gene is controlled by said PRV gene promoter and such that the resulting PRV mutant of step (4) expresses said foreign gene;

(3) Co-transfecting the hybrid plasmid of step (2) with infectious DNA from a pseudorabies virus such that homologous recombination between the infectious DNA and the plasmid of step (2) occurs through common DNA sequences flanking the insertion of the plasmid of step (2);

(4) Selecting or screening for a PRV mutant which expresses the gene product of said foreign gene, so as to produce a pseudorabies virus based viral vector which expresses said foreign gene.

In a preferred embodiment there is an additional step which is carried out prior to or after step (4) comprising selecting or screening for a PRV mutant which fails to produce the gene product of said non-essential PRV DNA sequence such that the resulting PRV mutant of the present invention also fails to produce the gene product of the non-essential PRV DNA sequence.

BRIEF DESCRIPTION OF THE DRAWINGS

FIG. 1) at the BamHI site of pBR322. Next, BglII linkers were added at the StuI sites of plasmid pBUK:BglII-B (at about 11 and 21 map units) and the resulting BglII/StuI fragment was then transferred to the BamHI site of pBR322 plasmid to produce plasmid pBUK:Stu12. Plasmid pBUK:Stu12 was cleaved with PstI and a 4.0 Kbp PstI fragment containing the PRV g92 gene was transferred to the PstI site of pBR322 to produce plasmid pBUK:Stu12/PstI.

In FIGS. 2–4 herein a solid line indicates PRV DNA sequences; a hatched bar indicates pBR322 DNA sequences; a large solid bar indicates the PRV g92 gene sequences with a small solid bar indicating the PRV g92 gene promoter sequences; and an open bar indicates the *E. coli* lacZ DNA sequences.

DETAILED DESCRIPTION OF THE INVENTION

Figure 1:
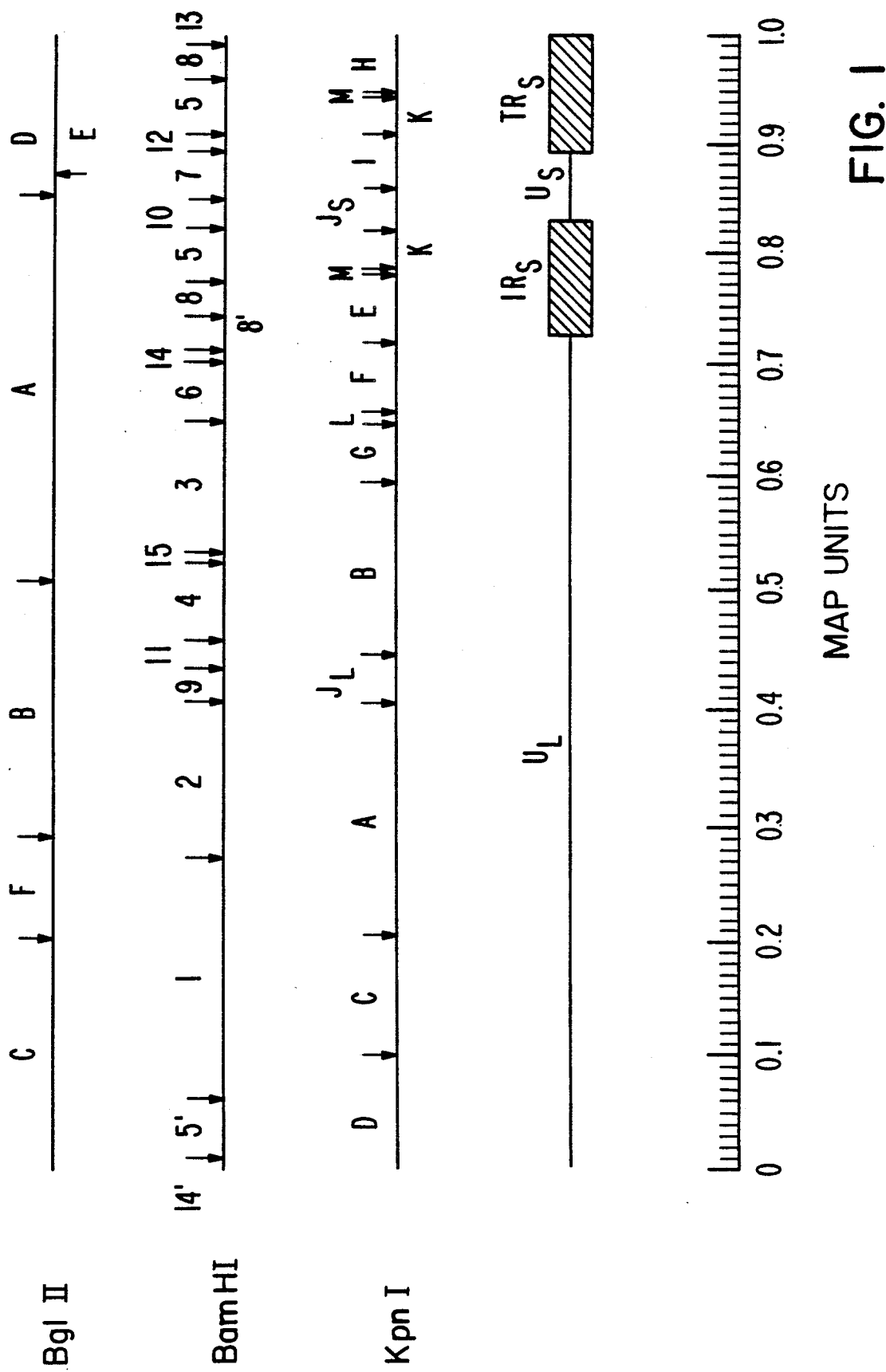
FIG. 1 illustrates the BglII BamHI and KpnI restriction nuclease maps for the DNA of virulent pseudorabies virus strains. The inverted repeat ($IR_S$) and terminal repeat ($TR_S$) regions which bracket the unique-short ($U_S$) region of the genome are shown. In addition, the unique long ($U_L$) region of the genome is shown.

As described above, in an embodiment of the present invention, the above-described objects have been met by a PRV which fails to produce any functional thymidine kinase as a result of an insertion in the tk gene, and a vaccine for pseudorabies disease comprising:

(1) a pharmaceutically acceptable amount of said virus; and (2) a pharmaceutically acceptable carrier or diluent.

In a further embodiment of the present invention, the PRV also fails to produce any glycoprotein gI as a result of a mutation in the gI gene.

In another embodiment of the present invention, the PRV is a temperature-resistant virus.

In still another embodiment of the present invention, the above-described objects have been met by a process for producing a PRV which fails to produce any functional thymidine kinase as a result of an insertion in the tk gene comprising:

(1) Constructing a hybrid plasmid comprising a cloning vector and a DNA fragment of PRV containing substantially all of the PRV tk gene and flanking sequences thereof;

(2) Inserting a foreign DNA sequence within the coding region of the PRV tk gene of the hybrid plasmid of step (1);

(3) Co-transfecting, in PRV host cells the hybrid plasmid of step (2) with infectious DNA from a tk$^+$ pseudorabies virus;

(4) Selecting, in tk$^-$ PRV host cells, for tk$^-$ PRV from the virus produced in step (3) so as to produce a PRV mutant which fails to produce any functional thymidine kinase as a result of an insertion in the tk gene.

In a preferred embodiment, prior to or during step (2), a functional PRV gene promoter is inserted into the PRV tk gene of the hybrid plasmid of step (1) and, in step (2), a foreign gene is inserted adjacent to said PRV gene promoter such that the expression of said foreign gene is controlled by said PRV gene promoter and such that the resulting PRV mutant of step (4) expresses said foreign gene. In this embodiment, prior to step (4) or after step (4) there is an additional step comprising screening or selecting for PRV which express said foreign gene so as to produce a PRV mutant which fails to produce any functional thymidine kinase as a result of an insertion in the tk gene and expresses said foreign gene.

In an additional embodiment of the present invention, the above-described objects have been met by a pseudorabies virus based viral vector comprising pseudorabies virus having inserted therein a foreign gene adjacent to a PRV gene promoter such that the expression of said foreign gene is controlled by said PRV gene promoter.

In another embodiment of the present invention, the above-described objects have been met by a pseudorabies virus based viral vector produced by the process comprising:

(1) Constructing a hybrid plasmid comprising a cloning vector and a DNA fragment of PRV containing substantially all of a non-essential PRV DNA sequence and flanking sequences thereof;

(2) Inserting a PRV gene promoter and a foreign gene adjacent to said PRV gene promoter within the non-essential PRV DNA sequence of the hybrid plasmid of step (1) such that the expression of said foreign gene is controlled by said PRV gene promoter and such that the resulting PRV mutant of step (4) expresses said foreign gene;

(3) Co-transfecting the hybrid plasmid of step (2) with infectious DNA from a pseudorabies virus such that homologous recombination between the infectious DNA and the plasmid of step (2) occurs through common DNA sequences flanking the insertion of the plasmid of step (2);

(4) Selecting or screening for a PRV mutant which expresses the gene product of said foreign gene so as to produce a pseudorabies virus based viral vector which expresses said foreign gene.

In a preferred embodiment, there is an additional step which is carried out prior to or after step (4) comprising selecting or screening for a PRV mutant which fails to produce the gene product of said non-essential PRV DNA sequence such that the resulting PRV mutant of the present invention also fails to produce the gene product of the non-essential PRV DNA sequence.

As used herein, a "foreign DNA sequence" means (1) any DNA sequence which does not encode a gene, i.e., a non-coding DNA sequence regardless of origin, such as a viral eucaryotic, or procaryotic non-coding sequence and inclusive of oligonucleotide linkers; (2) any DNA sequence which encodes a gene other than a PRV gene and which is not an equivalent of the gene in which the insertion is made e.g., if the insertion is in the PRV tk gene, the DNA sequence may not be a viral, eucaryotic or procaryotic tk gene, or (3) any coding PRV DNA sequence which has been translocated from its normal location on the PRV genome to another location on the PRV genome, such as the PRV g92 gene translocated into the PRV tk gene.

As used herein a "foreign gene" means (2) and (3) above for the definition of a "foreign DNA sequence". The preferred "foreign gene" is (2) above for the definition of a "foreign DNA sequence".

The foreign gene which can be employed in the present invention is not critical thereto and can by the *E. coli* lacZ gene and the transposon Tn5 gene (neo$^R$) in addition to complete or partial genes for antigens or antigenic portions thereof, of causative agents of infectious animal diseases such as porcine parvovirus, transmissible gastroenteritis, atrophic rhinitis, scours, foot and mouth disease rabies, hog cholera, rotavirus, and others.

For example foreign genes which can be employed are those which code for surface proteins, i.e., antigens, which elicit neutralizing antibodies and immunity against enveloped viruses which are significant pathogens of swine, such as the influenza hemagglutinin gene (see: Smith G. L., Murphy, B. R., Moss, B., *Proc. Natl. Acad. Sci., USA* 80:7155 7159 (1983)); the vesicular stomatitis virus G gene (see: Mackett, M., Yilma, T., Rose, J. K., Moss, B., *Science* 227:433–435 (1985)); the rabies virus G gene (see: Viktor, T. J., MacFarlan, R. I., et al, *Proc. Natl. Acad. Sci.* 81:7194–7198 (1984)); and the transmissible gastroenteritis virus gp195 gene (see: Hu, S., Bruszewski, J., Smalling, R., *Vaccinia Viruses as Vectors for Vaccine Antigens*, Quinnan Eds., Elsevier Science Publishing Co. (1985), pages 201–208)

In addition, foreign genes which can be employed are those which code for surface proteins, i.e., antigens, which elicit neutralizing antibodies and immunity against non-enveloped viruses which are significant pathogens of swine, such as foot and mouth disease virus capsid protein VPI gene (see: Weddell, G. N., Yansura, D. G., Dowbenko, D. J., Hoatlin, M. E., Grubman, M. J., Moore, D. M., Kleid, D. G., *Proc. Natl. Acad. Sci., USA* 82:2618–2622 (1985)); and porcine parvovirus capsid protein B and C genes (see: Smith, S., Halling, S. M., *Biotech.* 3:715–720 (1985)).

The specific selection means for selecting for the presence or absence of a functional TK. i.e., tk+ or tk− viruses is not critical to the present invention. Examples of the selection means for a tk+ virus include: growth medium supplemented with $10^{-4}$M hypoxanthine, $10^{-6}$M aminopterin $4 \times 10^{-5}$M thymidine and $10^{-5}$M glycine (hereinafter "HATG") (see: Dubbs, D. R., Otsuka, H., Qavi, H. and Kit, S., *Virol.* 126:408 411 (1983)) and growth medium supplemented with $6 \times 10^{-7}$M methotrexate; $1.6 \times 10^{-5}$M thymidine, $5 \times 10^{-5}$M adenosine, $5 \times 10^{-5}$M guanosine and $10^{-4}$M glycine (hereinafter "MTAGG") (see: Mungon, W., Kraiselburd, E., Davis, D. and Mann, J., *J. Virol.* 7:813–820 (1971)). Examples of the selection means for a tk− virus include: growth medium containing 25 μg/ml 5-bromodeoxyuridine (hereinafter "BrdUrd"), growth medium containing 100 μg/ml 5-iododeoxyuridine (hereinafter "IdUrd") or growth medium containing 100 μg/ml arabinosylthymine. Many modifications of the nucleoside analog selection techniques for tk− viruses can also be used. For example, the virus infected cells can be grown in media with about 2.5 to 25 μg/ml BrdUrd. Since the BrdUrd is incorporated into DNA of tk+ viruses and BrdUrd-containing DNA is highly photosensitive the virus harvests can be treated with about 0.5 μM Hoechst 33258 to further photosensitize the DNA. The DNA is then exposed to "cool white" fluorescent light (General Electric, 15 w) for 4 min to deliver about 50 ergs/mm$^2$/sec (Hillary, A. M., Lugo, T. G. and Fournier, R. E. K., *Biochem. Genet.* 22:201–213 (1984)). Following this procedure, the infectivity of tk+ viruses is selectively destroyed while tk− viruses are resistant to this treatment.

As discussed above, the *E. coli* lacZ gene can be used as the foreign DNA sequence and can be fused to a PRV gene promoter such that the resulting chimeric gene is flanked on both the 5' and 3' sides by for example, the PRV tk DNA, in the thymidine kinase negative PRV insertion mutants of the present invention, in addition to, for example, the PRV g92 and the PRV gI gene, in the pseudorabies virus based viral vectors of the present invention. This insertion mutant can then be screened for by assaying recombinant PRV plaques expressing β-galactosidase, which is detected by the blue color produced by action of the enzyme upon X-Gal (Boehringer-Mannheim) (see: Chakrabarti, S., Brechling, K. and Moss, B., *Mol Cell. Biol.* 5:3403–3409 (1985)).

As discussed above, the transposon Tn5 gene (neo$^R$) can also be used as the foreign DNA sequence. This transposon encodes an aminoglycoside 3′-phosphotransferase and is capable of conferring resistance to neomycin and to the drug. G418 (see: pNeo; Pharmacia P-L Biochemicals). To obtain expression of the transposon Tn5 gene, it is necessary that the PRV gene promoter be positioned 5′ to the coding region of the transposon Tn5 gene. (see: Franke, C. A., Rice, C. M., Strauss, J. H. and Hruby, D. E., *Mol. Cell. Biol.* 5:1918–1924 (1985)).

The viruses of the present invention which express complete or partial genes for antigens or antigenic portions thereof as foreign genes can be screened for by standard immunological procedures. A convenient and rapid procedure for identifying plaques formed by viruses expressing such foreign genes are well known (see: Holland, T. C., Sandri-Goldin, R. M., Holland, L. E., Marlin, S. D., Levine, M., Glorioso, J. C., *J. Virol.* 46:649–652 (1983)). In addition, the viruses of the present invention which express foreign antigens can be screened for by co-expression of a marker gene, such as the lacZ gene (see: Chakrabarti, S., Brechling, K., Moss, B., *Mol. and Cell. Biol.* 3403–3409 (1985)).

In the process for producing a pseudorabies based viral vector and in the preferred embodiment of the PRV tk− insertion mutant, i.e., wherein a foreign gene is inserted in the tk gene "selection means" or "screening means" can be employed. Whether "selection means" or "screening means" is employed will depend on the non-essential PRV DNA sequence within which the insertion is made. For example if the non-essential PRV DNA sequence encodes an antigen such as PRV gI or PRV g92, "screening means" are employed. On the other hand, if the non-essential PRV DNA sequence within which the insertion occurs is the PRV tk gene, "selection means" are employed. In addition, whether "selection means" or "screening means" is employed will depend upon the foreign gene used as the insertion. For example, if the foreign gene to be inserted is, e.g., the lacZ gene or an antigen gene, "screening means" will be employed. On the other hand, if the foreign gene is a dominant marker, for example, a tk gene (a PRV tk gene or other viral, eucaryotic or procaryotic tk gene) or the (neo$^R$) gene, "selection means" will be employed.

As used herein, "selection means" refers to the enrichment of the fraction of a desired recombinant virus in the total virus population. Further, as used herein "screening means" refers to the identification of the desired recombinant within the total virus population.

Selection means are preferred when used alone, or prior to screening means when used in combination therewith. This is because the resulting enrichment for the desired recombinant viruses due to the use of selection means reduces the amount of screening required to obtain the recombinant viruses.

As discussed above, in the selection means, a dominant marker such as the (neo$^R$) gene, may be employed to select for recombinant viruses with insertions in any non-essential PRV DNA sequence, regardless of whether the parental PRV is tk$^+$ or tk$^-$. On the other hand, when the dominant marker is a tk gene, only tk$^-$ parental PRV may be employed since such allows for selection of tk$^+$ PRV.

Thus, in the present invention, it is also possible to select or screen for the gene product produced by the foreign gene insertion so as to obtain thymidine kinase negative PRV insertion mutants and pseudorabies virus based viral vectors which express the foreign gene.

As discussed above, non-coding foreign DNA sequences include oligonucleotide linkers. The size of the oligonucleotide linkers is not critical to the present invention. Generally the size of the oligonucleotide linkers is 8–10 nucleotides in length, but can be longer, e.g., about 50 nucleotides, or shorter, e.g., 4, 5 or 7 nucleotides. The preferred length of the oligonucleotide linker is about 8 to 10 nucleotides in length. The DNA sequence of the oligonucleotide linker is also not critical to the present invention.

Similarly, the size and sequences of other foreign DNA sequences employed in the present invention is not critical. Generally, the size of foreign DNA sequences, other than oligonucleotide linkers, is about 0.5 to 5 Kbp in length. For example, the (neo$^R$) gene is about 1.0 Kbp in length and the *E. coli* lacZ gene is about 3.0 Kbp in length.

As used herein, a "non-essential PRV DNA sequence" means a region of the PRV genome which is not required for viral replication, i.e., a non-essential PRV gene or a non-coding region of the PRV genome. The preferred non-essential PRV DNA sequence is a non-essential PRV gene.

The non-essential PRV DNA sequence employed in the present invention is not critical thereto.

Examples of such non-essential PRV DNA sequence include the PRV tk gene discussed above, the PRV g92 gene (see: Robbins, A. K., Watson, R. J., Enquist, L. W., European Patent Publication 0 162 738), and the PRV gI gene (see: Mettenleiter, T. C., Lukacs, N., and Rziha, H. J., *J. Virol.* 53:52–57 (1985); and Mettenleiter, T. C., Lukacs, N., and Rziha, H. J., *J. Virol.*, 56:307–311 (1985)). The preferred non-essential PRV gene is the PRV tk gene because thymidine kinase negative mutants are attenuated and preferred as vaccines.

As used herein, "flanking sequences" means the sequences upstream, downstream, or both upstream and downstream, from the non-essential PRV DNA sequence, e.g., the PRV tk gene coding sequences. The upstream sequences for the non-essential PRV gene contain the transcriptional control signals, i.e., promoters and enhancers, whereas the downstream sequences contain the transcription termination and polyadenylation signal of, for example, the PRV tk gene.

The method of inserting the foreign DNA sequence into plasmid DNA will depend upon the type of foreign DNA sequence used and/or the sequence of the gene in which it is to be inserted. Palindromic double stranded linkers containing one or more restriction nuclease sites in the oligonucleotide sequence (New England Biolabs, Inc.) may be inserted by well known procedures (see: Maniatis, T., Fritsch and E. F., Sambrook, J., *Molecular Cloning,* Cold Spring Harbor Laboratory (1982)). Foreign DNA sequences may also be inserted into plasmid DNA by tailing ends with complementary homopolymers using terminal transferase (see: Maniatis, T., Fritsch, E. F. and Sambrook, J., *Molecular Cloning,* Cold Spring Harbor Laboratory (1982)).

The specific PRV gene promoter employed in the present invention is not critical thereto and can include, for example, the PRV g92 promoter and the PRV tk gene promoter.

Figure 3:
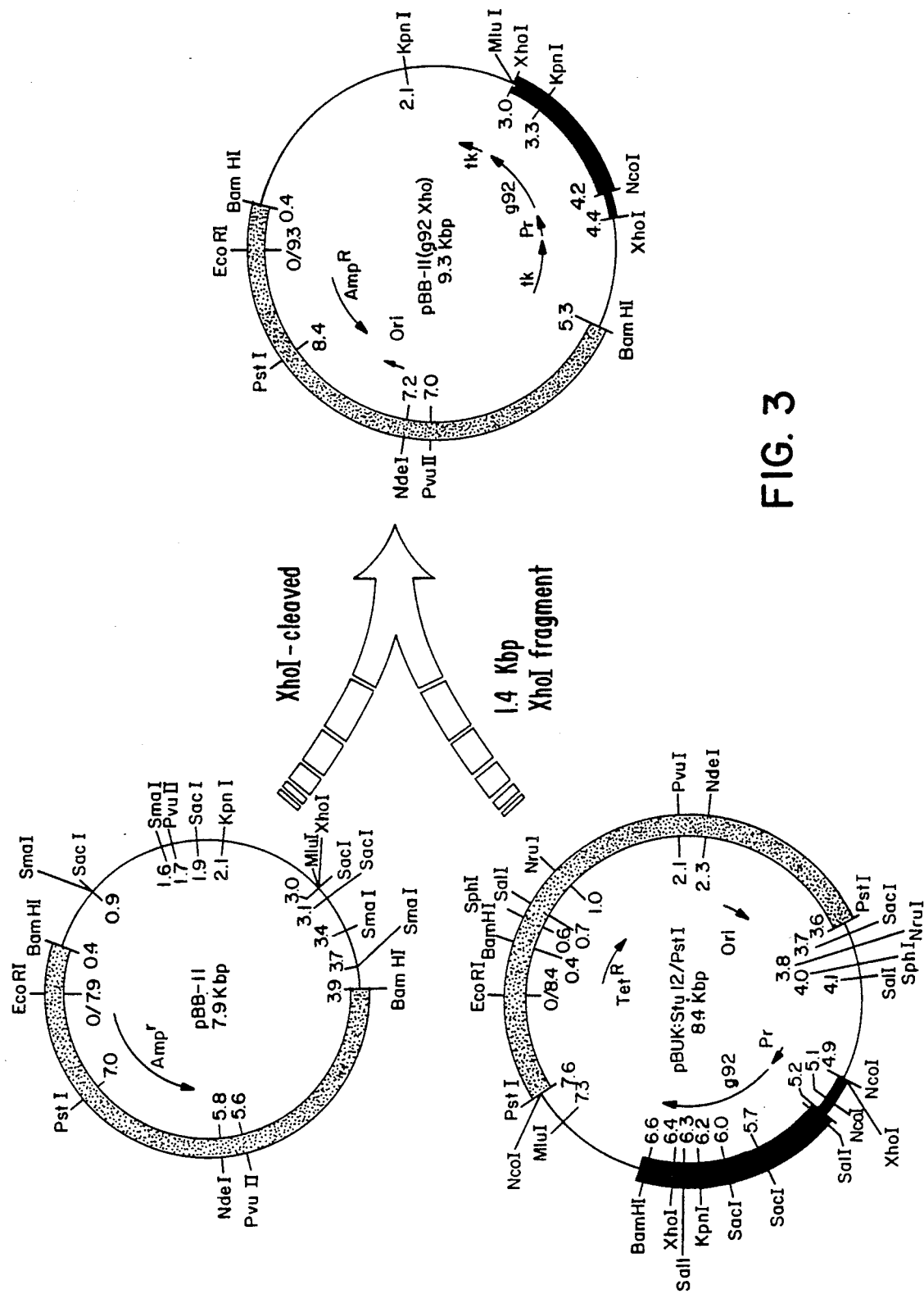
FIG. 3 schematically illustrates, by example, the derivation of pBB-11(g92Xho) from pBUK:Stu12/PstI and pBB-11. pBB-11 comprises the BamHI fragment of PRV(BUK-7) inserted into the single BamHI site of pBR322. pBB-11(g92Xho) was constructed by cloning the 1.4 Kbp XhoI PRV g92 gene fragment from pBUK:Stu12/PstI at the XhoI site (3.0 map units) of pBB-11.
Figure 4:
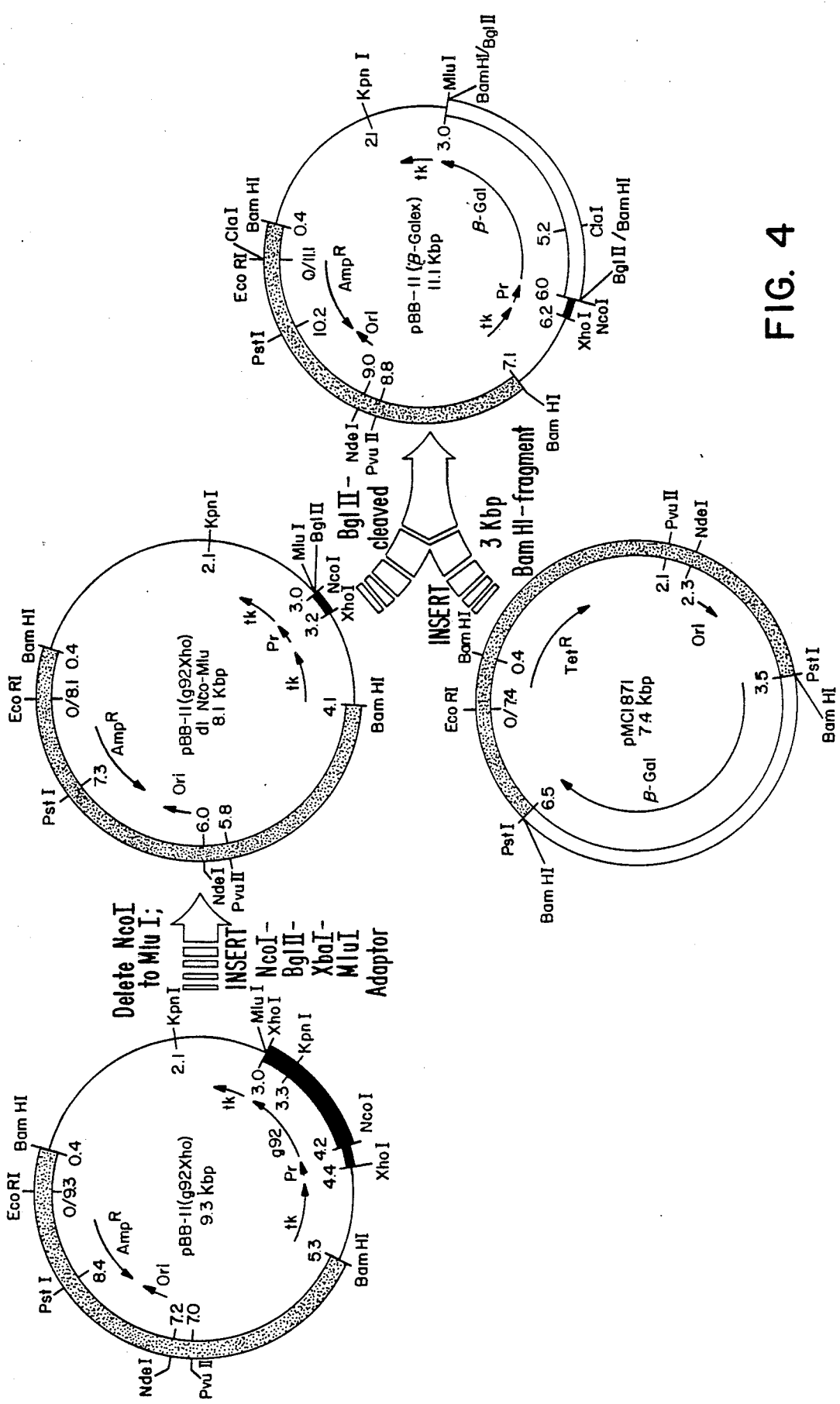
FIG. 4 schematically illustrates, by example, the derivation of pBB-11(g92Xho)dl Nco-Mlu and pBB-11(β-Galex). pBB-11(g92Xho)dl Nco-Mlu was constructed by cleaving pBB-11(g92Xho) at the NcoI site (4.2 map units), ligating a oligonucleotide adaptor containing a NcoI cohesive end, BglII and XbaI cleavage sites, and a MluI cohesive end, at the NcoI end of pBB-11(g92XhoI), cleaving the plasmid with MluI to excise the 1.2 Kbp NcoI-XhoI PRV g92 sequence from pBB-11(g92Xho) in addition to 10 bp of the PRV tk sequence, and finally ligating the MluI cohesive ends to circularize the plasmid designated pBB-11(g92Xho)dl Nco-Mlu. This plasmid contains the PRV g92 promoter inserted in the PRV tk gene. pBB-11(β-Galex) was constructed by cleaving the adaptor sequence of pBB-11(g92Xho)dl Nco-Mlu at the single BglII site, and inserting a 3 Kbp BamHI lacZ fragment (β-Gal) derived from plasmid pMC1871 (see: Casadaban, M. J., *Methods in Enzymology* 100:293 (1983)) at the BglII site of pBB-11(g92Xho)dl Nco-Mlu.

The PRV g92 gene promoter can be derived from the hereinafter described tk$^+$ PRV strains as well as tk$^-$ PRV strains such as PRV(BUK-5A) (ATCC No. VR-2028) and PRV(BUK-dl 3) (ATCC No. VR-2074) all of which produce g92. The PRV g92 gene promoter is located within the NcoI to XhoI fragment of the PRV g92 gene (see: FIG. 3 and FIG. 4). The PRV tk gene promoter can be derived from any of the hereinafter described tk$^+$ PRV strains.

Foreign DNA sequences inserted into the PRV tk gene and other non-essential PRV DNA sequence will only be expressed as a functional protein if the appropriate gene expression control signals are present. These signals consist of two types; those that control levels of mRNA and those that control efficiency of mRNA translation into protein.

The levels of mRNA are determined by transcription rates, mRNA processing efficiency, and mRNA degradation rates. Relatively little is currently understood about the molecular control of the latter two parameters; however, the control signals which regulate transcription are better defined. Transcription, which is the process whereby mRNA is synthesized off a DNA template, occurs through interaction of RNA polymerase, and accessory protein factors with particular DNA sequences of the template. The sets of DNA sequences which bind RNA polymerase and control the site and onset of initiation of mRNA are collectively referred to as the promoter region.

The efficiency of translation of the mRNA is determined by the sequence and length of the leader mRNA fragment which precedes the start codon of the coding sequence and by the presence of a short consensus sequence flanking the start codon called "Kozak's" sequence. There is great variation in the DNA sequences of promoters for different genes from a variety of species. Even within the herpesvirus genome, there are few if any recognizable common features within the DNA sequences of different viral gene promoters. Detailed functional studies of several eucaryotic promoters have demonstrated the common occurrence of canonical consensus sequences, the TATA site which determines the point of initiation of the mRNA, and the CAAT box, which effects transcription efficiency. In addition, there are upstream distal signals which further modulate transcription efficiencies.

The herpes simplex virus tk gene promoter has the canonical consensus signals described above, however, they are absent from the PRV tk gene promoter sequences upstream from the site of mRNA initiation.

Foreign DNA sequences containing coding open reading frames that are inserted into the PRV tk gene may be expressed as fusion proteins off of the PRV tk gene promoter if the inserted coding sequence is in phase with the PRV tk gene coding sequence, and if no stop codons are interposed. However, viral vectors of this type are not preferred because the PRV tk gene promoter is "weak", producing low levels of mRNA;

and because fusion proteins are often less immunogenic than native forms.

The DNA sequence of the envelope protein coded by the PRV g92 gene has been determined (see: Robbins, A. K., Watson, R. J., Enquist, L. W., European Patent Publication 0 162 738) and some putative control signals of the PRV g92 gene have been identified by virtue of a loose similarity with the canonical consensus sequences of promoters. However, the actual promoter has not been defined functionally prior to this invention. A functional promoter is essential to the expression of a foreign gene by a viral vector. The PRV g92 gene promoter is the preferred PRV gene promoter for three reasons. First, optimal gene expression during the lytic infection of the PRV growth cycle occurs off of PRV promoters. Cellular promoters and many other viral promoters are suppressed by PRV factors which redirect mRNA synthesis solely towards the production of PRV proteins. Secondly, the PRV g92 gene promoter directs the abundant synthesis of mRNA. Third, the PRV DNA fragment containing the PRV g92 gene promoter utilized here, i.e., a 0.2 Kbp XhoI to NcoI fragment at map units 4.9 to 5.1 of pBUK:Stu12/Pst1, has a NcoI site at the initiation site of the coding sequence for the protein coded by the PRV g92 gene. Foreign genes may be inserted at this site using appropriate adaptors and be translated as efficiently as the PRV g92 protein. This is because the recombinant construction retains the Kozak's consensus sequence, in correct position relative to the mRNA cap site. The adaptor employed will of course depend upon the DNA sequence of the foreign gene. Also, foreign genes may be expressed off of the NcoI sites ATG start codon as authentic proteins, rather than fusion proteins: thereby preserving protein immunogenicity.

In addition, production of mRNA employs the presence of transcription termination and polyadenylation signals. Eucaryotic transcription termination signals are at present poorly defined. However, polyadenylation signals are known to contain the consensus sequence "AATAAA". The pseudorabies virus based viral vectors of the invention can utilize the polyadenylation and downstream transcription termination signals of the PRV tk gene adjacent to the insert; thereby assuring correct termination and polyadenylation of the mRNA of the inserted foreign DNA.

Figure 5:
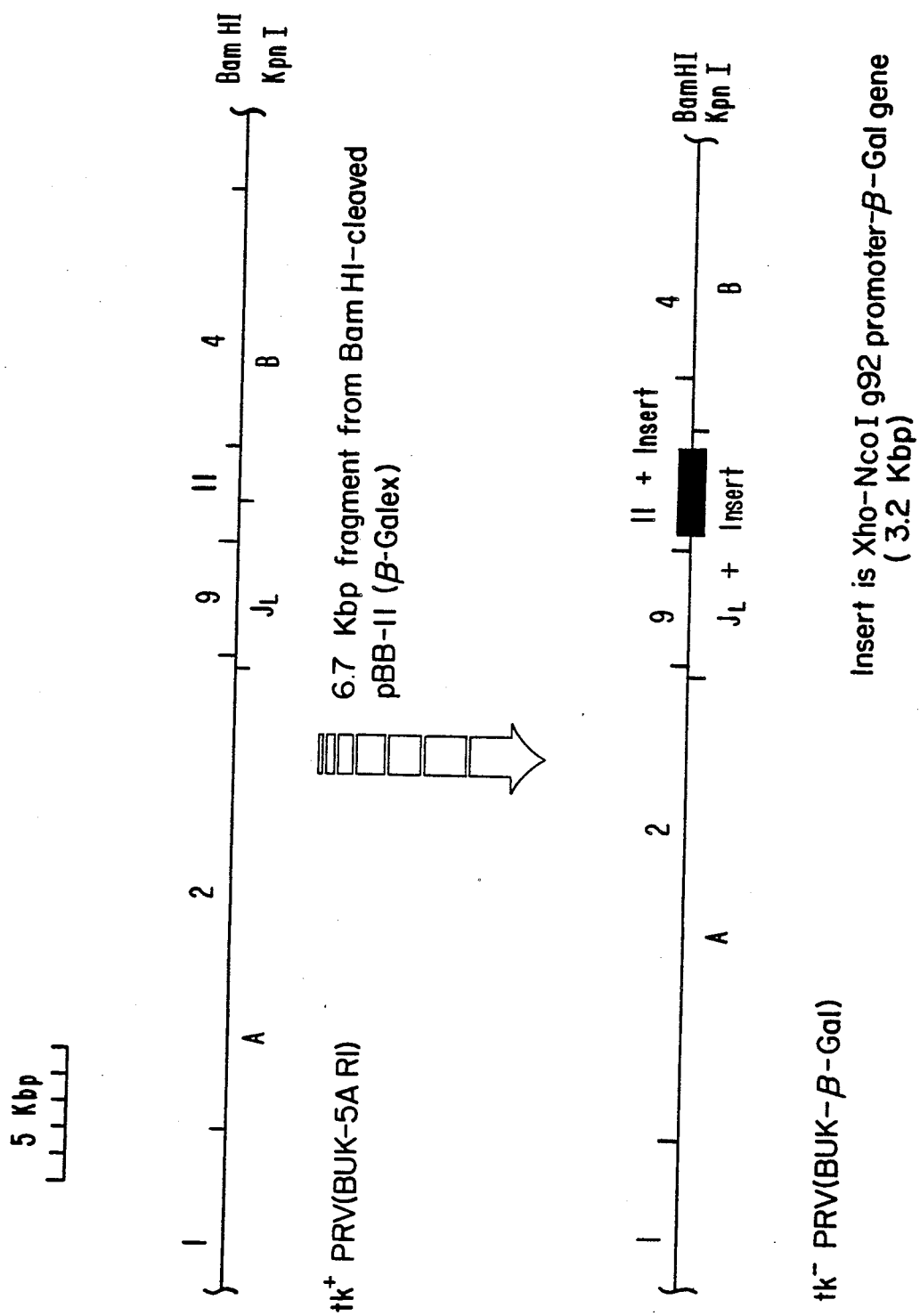
FIG. 5 schematically illustrates, by example, the derivation of the tk$^-$ PRV insertion mutant, PRV(BUK-β-Gal). which expresses the *E. coli* lacZ gene from the PRV g92 promoter. Rab-9 cells were co-transfected with infectious DNA from tk$^+$ PRV(BUK-5A R1) and BamHI-cleaved plasmid pBB-11(β-Galex). Virus harvests from the co-transfection were enriched for tk$^-$ PRV recombinants by passage in Rab(BU) cells in growth media containing 100 μg/ml 5-iododeoxyuridine. Viral harvests were then titrated in Rab-9 cells, candidate plaques expressing β-galactosidase were isolated and propagated in Rab-9 cells. Viral DNAs prepared from the candidate plaques were analyzed with restriction nucleases to identify those with the 3 Kbp lacZ inserts. The candidate viruses were then analyzed to verify that they failed to produce a functional thymidine kinase.

The particular site of insertion into the PRV tk gene is not critical and can be made in, for example, any of the over 50 different restriction nuclease sites predicted from the nucleotide sequence of the PRV tk gene (see: FIG. 5 of U.S. Pat. No. 4,514,497) or in new restriction sites created by well known procedures. For example, SacI sites are predicted from the sequence at nucleotides 115, 925, 1007, 1034 and 1073. SmaI sites are predicted at nucleotides 4, 402 and 763 and XhoI and MluI sites are predicted at nucleotides 1100 and 1110. respectively. In PRV(BUK-β-Gal) described below, the PRV g92 gene promoter and lacZ gene are inserted at the XhoI restriction nuclease site of the PRV tk gene (see: FIG. 3 and FIG. 4). By the judicious choice of foreign DNA sequence length, frame shift mutations may be produced in the tk gene, augmenting the effect of insertions within the tk gene.

Similarly, in the pseudorabies virus based viral vector embodiment of the present invention, the insertion site is not critical as long as the insertion site does not inactivate a gene required for viral replication, i.e., the insertion is within a non-essential PRV DNA sequence. The thymidine kinase negative PRV insertion mutant expressing the E. coli lacZ gene described below, i.e., PRV(BUK-β-Gal), is illustrative of the pseudorabies virus based viral vectors of the present invention.

The particular cloning vector employed in the present invention to construct the hybrid plasmid comprising a DNA fragment of PRV containing substantially all of the non-essential PRV DNA sequence, e.g., the PRV tk gene, and flanking sequences thereof of step (1) is not critical as long as the cloning vector contains a gene coding for a selective trait, e.g., drug resistance. Examples of such cloning vectors include pBR322 and pBR322-based vectors (see Sekiguchi, T., Nishimoto, T., Kai, R. and Sekiguchi, M., *Gene* 21:267–272 (1983)), pMB9, pBR325, pKH47 (Bethesda Research Laboratories), pBR328, pHC79 (Boehringer Mannheim Biochemicals), phage Charon 28 (Bethesda Research Laboratories), pKB11, pKSV-10 (P-L Biochemicals), pMAR420 (see: Otsuka, H., Hazen, M., Kit, M., Qavi, H. and Kit, S., *Virol.* 113:196–213 (1981)) and oligo (dG)-tailed pBR322 (New England Nuclear)).

pBR322 is a preferred cloning vector employed in the present invention since the PRV(BUK) BamHI-11 fragment was found to contain the PRV tk gene and pBR322 only has one BamHI cloning site (see: U.S. Pat. No. 4,514,497). Insertion of a DNA fragment at this site inactivates the cloning vector's tetracycline gene, but not the ampicillin gene, so that tetracycline-sensitive, ampicillin-resistant hybrid plasmids that are larger than pBR322 due to the insertion can easily be isolated.

Besides BamHI fragments, BglII, BclI and MboI fragments of the PRV can be cloned at the BamHI site of pBR322 because BglII, BclI and MboI fragments have the same cohesive ends as BamHI fragments. pMB9, pBR325, pKH47, pBR328, pHC79 and phage Charon 28 DNA also have a single BamHI cloning sites. However, the MboI fragments are smaller and contain only part of the tk gene, while the BglII fragments are too large to be conveniently cloned in any of the cloning vectors except for phage Charon 28.

It has also been found that the PRV(BUK) KpnI-$J_L$ fragment contains the PRV tk gene (see: U.S. Pat. No. 4,514,497). Thus, pKB11, pKSV-10 and pMAR420 are useful cloning vectors for cloning this fragment since they have only one KpnI cloning site. Similarly, oligo (dG)-tailed pBR322 can be employed as a cloning vector with an oligo (dC)-tailed KpnI-$J_L$ fragment PRV.

The specific host employed for growing the hybrid plasmids of the present invention is not critical to the present invention. Examples of such hosts include E. coli K12 RRI (see: Bolivar, F., Rodriguez, R. L., Greene, P. J., Betlach, M. C., Heyneker, H. L., Boyer, H. W., Crosa, J. H. and Falkow, S., *Gene* 2:95–113 (1977)); E. coli K12 HB101 (ATCC No. 33694); E. coli MM21 (ATCC No. 336780); and E. coli DH1 (ATCC No. 33849). E. coli K12 RR1 is the preferred host and has an F$^-$ hsd R hsd M genotype.

Similarly, alternative vector/cloning systems can be employed such as plasmid vectors which grow in E. coli or *Saccharomyces cerevisiae*, or both, or plasmid vectors which grow in B. subtilus, or even vectors such as bovine papilloma virus (ATCC No. 37112) which grow in animal cells such as mouse (ATCC No. RL1616) (see: Elder, J. T., Spritz, R. A. and Weissman, S. M., *Ann. Rev. Gen.* 15:295–340 (1981) and Ure, R., Grossman, L. and Moldave, K., *Methods in Enzymology* "Recombinant DNA" Vol. 101, Part C, Academic Press, N.Y. (1983)).

The precise PRV tk gene sequences which must be present in the hybrid plasmids of steps (1) and (3) of the thymidine kinase negative PRV insertion mutant embodiment of the present invention will depend on the sequences chosen to be inserted and the restriction nucleases to be employed in the engineering of the insertion mutant.

The specific PRV DNA sequences adjacent to the insertion in the plasmid required in steps (1) and (3) of the thymidine kinase negative PRV insertion mutant embodiment of the present invention will depend on the specifics of the insertion in the hybrid plasmid. In general, the size of the PRV DNA sequences adjacent to both the 3' and 5' sides of the insertion will be at least about 400 bp. In pBB-11($\beta$-Galex) (see: FIG. 2). described in detail below, the 3' and 5' sequences on both sides of the insertion were 2.6 Kbp and 0.9 Kbp in length, respectively.

The specific tk+ PRV strain employed as a starting material in the present invention from which the PRV DNA fragment containing the non-essential PRV DNA sequence, e.g., the PRV tk gene of step (1) and the tk+ infectious PRV DNA of step (3) of the thymidine kinase negative PRV insertion mutant embodiment of the present invention are obtained is not critical. Similarly, the specific tk+ PRV strain employed as a starting material for the pseudorabies virus based viral vector is not critical to the present invention. Examples of such strains include the well-known attenuated strains such as the Bucharest strain, the SUCH-1 strain (see: Skoda, R., Brauner, I., Sadecky, E. and Mayer, V., *Acta Virol.* 8:1-9 (1964)), the Norden strain (see: Paul, P. S., Mengeling, W. L. and Pirtle, E. C., *Arch. Virol.* 73:193-198 (1982)) and PRV(BUK-5A R1) (see: U.S. Pat. No. 4,514,497); and virulent strains isolated directly from diseased animals or passaged frequently in the laboratory such as the Aujeszky strain (ATCC No. VR-135), the P-2208 strain, the KC-152D strain (see: Maes, R. K., Kanitz, C. L. and Gustafson, D. P., *Am. J. Vet. Res.* 44:2083-2086 (1983)), the S62/26 Iowa strain, the Ind-F strain, the Ind-S strain, the Ind-R strain and the Shope strain (see: Paul, P. S., Mengeling, W. L. and Pirtle, E. C., *Arch. Virol.* 73:193-198 (1982)). If the insertion is to be made in a non essential PRV sequence other than the PRV tk gene it is preferable that the PRV strain employed for recombination be a vaccine strain such that the resulting insertion mutant will possess the attenuated properties of the vaccine strain. The Bucharest strain is the preferred tk+ PRV strain from which the PRV DNA fragment containing the tk gene of step (1) is derived while PRV(BUK-5A R1) is the preferred tk+ PRV from which the infectious PRV DNA of step (3) is derived from the thymidine kinase negative PRV insertion mutant embodiment of the present invention. PRV(BUK-5A R1) is preferred because it was derived from the attenuated Bucharest strain and has been further attenuated by the introduction of mutagen induced mutations such that the resulting PRV mutant of step (4) possesses the mutations found in PRV(BUK-5A R1). Similarly, the Bucharest strain is the preferred strain employed as a starting material for obtaining the pseudorabies based viral vectors of the present invention.

tk− PRV strains can also be employed as a starting material for the pseudorabies virus based viral vectors. The specific tk− PRV strain employed is not critical to the present invention and can include PRV-TK−(101) (see: McGregor, S., Ecstendy, B. C., Kaplan, A. S. and Ben-Porat, T., *Am. J. Vet. Res.* 46:1494-1497 (1985)), in addition to the temperature-resistant mutagen-induced mutant PRV(BUK-5A) (ATCC No. VR-2028) the temperature-resistant and the deletion mutants. PRV(BUK-dl 3) (ATCC No. VR-2074) and PRV(dltk/dlg92) (ATCC No. VR-2116). PRV(dltk/dlg92) is the preferred tk− PRV strain employed as the starting material for the pseudorabies based viral vectors of the present invention because it contains a deletion in the PRV tk gene such that it fails to produce any functional thymidine kinase, it contains a deletion in the PRV g92 gene such that it fails to produce any antigenic g92 polypeptides and it contains a deletion in the PRV gI gene.

The particular PRV host cells employed in the present invention will depend on the inserted foreign DNA sequence employed. That is, to select for or against a tk gene, tk− PRV host cells should be employed. However, to select for a functional $neo^R$ gene or lacZ gene, either tk+ or tk− PRV host cells can be employed since neither naturally produce the $neo^R$ or lacZ gene products. To select for other foreign genes either tk+ or tk− PRV host cells can also be employed with the only limitation being that the host cells employed do not produce the gene product of the inserted foreign gene.

In co-transfecting step (3) of the thymidine kinase negative insertion mutant embodiment of the present invention, either tk+ or tk− host cells can be employed, although tk+ PRV host cells are preferred because the desired tk− recombinant virus grow more efficiently in tk+ PRV host cells.

The specific tk+ host cells employed in the present invention are not critical as long as they allow for permissive growth of PRV. Examples of such tk+ host cells include Rab-9 (rabbit skin cells) having ATCC No. 1414; primary rabbit kidney cells; secondary rabbit kidney cells; monkey cells, e.g., CV-1 and OMK; human cells, e.g., HeLa(S3) and human embryonic kidney cells; and chick embryo fibroblast cells. RAB-9 are the preferred tk+ host cells employed in the present invention. However, it should be noted that for the production of virus to be used for vaccination of animals in the field, a United States Department of Agriculture certified cell line permissive for PRV, preferably of the same species as the animal to be vaccinated, and free of other infectious agents, should be used. For example, a suitable porcine cell line would be a certified diploid non-tumorgenic swine testicle (ST) cell line free of mycoplasma and other viruses.

The specific tk− host cells employed in the present invention are not critical as long as they allow for permissive growth of PRV. Examples of such tk− host cells include rabbit Rab(BU), mouse LM(TK−), human HeLa(BU25) (see: Kit, S., Dubbs, D. R. and Frearson, P. M., *Int. J. Cancer* 1:19-30 (1966); Kit, S., Dubbs, D. R., Prekarski, L. J. and Hsu, T. C., *Exp. Cell Res.* 31:297-312 (1963); Kit, S. and Qavi, H., *Virol.* 130:381-389 (1983); Kit, S., Qavi, H., Dubbs, D. R. and Otsuka, H., *J. Med. Virol.* 12:25-36 (1983)), syrian hamster BHK 21(TK− ) (see: Sandus, P. G., Wilkie, N. M. and Davidson, A. J., *J. Gen. Virol.* 63:277-295 (1982)), and human line 143 (see: Campione-Picardo, Rawls, W. E. and Bacchetti, S., *J. Virol.* 31:281-287 (1979)). Rab(BU) are the preferred tk− host cells employed in the present invention.

In the context of this invention, a temperature-resistant virus is a virus which is non-temperature sensitive. Thus, a temperature-resistant virus is capable of replicating at a non-permissive temperature, i.e., about 38.5°

C. to 40° C., preferably 39.1° C., about as well as the parental virus or field isolates of PRV replicate at a permissive temperature. By contrast, temperature-sensitive PRV strains contain mutations in viral genes essential for replication, whereby functional gene products are produced at permissive temperatures, i.e., about 32° C. to 37.5° C., preferably 34.5° C., but not at non-permissive temperatures. Therefore, in temperature-sensitive viruses, production of infectious virus particles is 4 to 7 logs lower at the non-permissive temperatures compared to production at permissive temperatures. With temperature-resistant virus strains production of infectious virus particles is about the same at non-permissive temperatures as at permissive temperatures.

Temperature-resistant viruses are superior to temperature-sensitive viruses as modified live virus vaccines because (1) attenuation results from alterations in pathogenic viral genes rather than from crippling viral genes required for replication; and (2) temperature-resistant viruses can be safely administered intramuscularly, intranasally or intravenously and can replicate in the deep tissues of the body so as to elicit a more complete and prolonged immunological response.

In contrast, temperature-sensitive viruses only replicate at low temperature sites, such as the upper respiratory tract, and thus, can only be administered intranasally.

The tk⁻ PRV insertion mutants of the present invention can be employed as modified live virus vaccines against pseudorabies diseases alone or when containing additional mutations which attenuate PRV. Such additional mutations include g92 mutations and gI mutations.

Alternatively, the tk⁻ PRV mutants of the present invention can be employed as killed virus vaccines against pseudorabies disease. That is, inactivation of infectivity by ultraviolet light or formaldehyde treatment of the tk⁻ PRV mutants yields a vaccine capable, after intraperitoneal administration, of eliciting cytotoxic T cells and protective antibodies against glycoproteins gIIa, gIIb, gIIc, gIII, gIV and gV. Animals immunized with this vaccine would thus be protected against virulent virus infections.

Furthermore, non-ionic detergent extracts (Nonidet P40 or Triton X-100) can be made from tk⁻ PRV mutant-infected pig cells to produce subunit PRV vaccines. After purification of the glycoproteins, they can be employed as subunit vaccines (see: Hilleman, M. R., Larson, V. M., Lehman, E. D., Salerno, R. A., Conard, P. G., McLean, A. A., In: *The Human Herpesvirus: An Interdiciplinary Perspective,* Eds. Nahmias, A. J., Dowdle, W. R. and Schinazi, R. F., (Elsevier, New York), page 503 (1981); Eisenberg, R. J., Ponce de Leon, M., Perevia, L., Long, D. and Cohen, G. H., *J. Virol.* 41:1099–1104 (1982); Long, D., Madara, T. J., Ponce de Leon, M., Cohen, G. H., Montgomery, P. C., Eisenberg, R. J., *Inf. Immun.* 37:761–764 (1984); and Dix, R. D. and Mills, J., *J. Med. Virol.* 17:9–18 (1985)).

As another alternative, the tk⁻ PRV mutants of the present invention can be employed as the tk PRV strain used as a starting material to obtain the g92 PRV mutants described in U.S. patent application Ser. No. 823,497 filed Jan. 28, 1986.

A pharmaceutically effective amount of the tk⁻ PRV mutants of the present invention can be employed along with a pharmaceutically acceptable carrier or diluent as a vaccine against pseudorabies disease in animals, such as swine, cattle, sheep and goats.

Examples of pharmaceutically acceptable carriers or diluents useful in the present invention include any phsiological buffered medium, i.e., about pH 7.0 to 7.4, containing from about 2.5 to 15% serum which does not contain antibodies to PRV, i.e., is seronegative for PRV. Agammaglobulin serum is preferred to serum which contains gammaglobulin. Examples of serum to be employed in the present invention include: swine serum, calf serum, fetal calf serum, horse serum and lamb serum. Agammaglobulin swine serum from pigs seronegative for PRV would be preferred for vaccination of swine and fetal calf serum or agammaglobulin calf serum would be preferred for vaccination of calves. Serum protein such as porcine albumin or bovine serum albumin in an amount of from about 0.5 to 3.0% can be employed as a substitute for serum. However, it is desirable to avoid the use of foreign proteins in the carrier or diluent which will induce allergic responses in the animal being vaccinated. Prior to lypholization, the virus may be diluted using any of the conventional stabilizing solutions containing phosphate buffered saline, glutamate, casitone or lactose hydrolyzate, sucrose, sorbose, lactose, gelatin and preservatives such as gentamicin, fungazone and amphotericin B.

It is preferred that the viruses of tee present invention be stored at a titer of at least $10^{5.5}$ to $10^{6.5}$ p.f.u./ml in a lypholized state at 4° C. to $-20°$ C. The lypholized virus may be reconstituted for use with sterile distilled water containing 1.0% (v/v) glycerol.

The useful dosage of the vaccine to be administered will vary depending upon the age, weight and species of the animal vaccinated and the mode of administration. As a live modified virus vaccine, a suitable dosage can be, for example, about $10^{4.5}$ to $10^{6.5}$ p.f.u., preferably about $10^{5.0}$ to $10^{6.0}$ p f.u. As a killed vaccine, a suitable dosage can be, for example, about 10 to 100 fold greater than that employed for a modified live virus vaccine.

The vaccines of the present invention can be administered intramuscularly and subcutaneously. Intramuscularly is the preferred mode of administration. The modified-live vaccines of the present invention can also be administered intranasally.

The following examples are provided for illustrative purposes only and are in no way intended to limit the scope of the present invention.

In the following examples, all media and buffer solutions were made up in glass distilled water unless otherwise indicated.

EXAMPLE 1

Production Of Insertion Mutants Of PRV

This example demonstrates a method for the production of a PRV insertion mutant that expresses a foreign gene during lytic infection of cells. The foreign gene used in this example is the lacZ gene of *E. coli*. However, as discussed above, other foreign genes and/or non-coding DNA sequences can be employed herein without departing from the spirit and scope of this invention. Expression of the lacZ gene from the PRV insertion mutant results in the production of the enzyme β-galactosidase, which in the presence of chromogenic substrates, converts the dye X-Gal (Boehringer-Mannheim) into a blue color. The PRV insertion mutant described herein is also a thymidine kinase negative PRV insertion mutant.

A. Purification of PRV DNA

PRV DNA was prepared essentially as described by Pignatti et al for the preparation of herpes simplex virus DNA (see: Pignatti, P. F., Cassai, E., Meneguzzi, G., Chemciner, N., and Milanesi, G. *Virol.* 93:260–264 (1979)).

More specifically, 20 8-oz prescription glass bottle monolayer cultures of Rab-9 (about $5 \times 10^6$ cells/culture) containing 20 ml of Eagle's minimal essential medium (AutoPow, APMEM, Flow Laboratories, Inc.) plus 10% (v/v) fetal calf serum, 50 µg/ml neomycin, 2.0 mM glutamine and 10 mM HEPES, pH 7.3 (hereinafter "growth medium") were infected at an m.o.i. of 5.0 PFU/cell with PRV(BUK-7). PRV(BUK-7) is a plaque purified clone of the well known and readily available Bucharest strain of PRV strain (see: U.S. Pat. No. 4.514.497). The infected cells were then incubated for 3 hr at 34.5° C. at which time cellular DNA synthesis had been inhibited by the viral infection. Then 1.0 µCi/ml and 0.25 µg/ml of $^3$H-thymidine was added to radioactively label the viral DNA and incubation was continued at 34.5° C. for 17 hr more. The cells were dislodged from the glass by scraping into the growth medium with a rubber policeman, centrifuged at $600 \times g$, washed with ice cold phosphate-buffered saline solution comprising 0.14M NaCl, 0.003M KCl, 0.001M $CaCl_2$, 0.0005M $MgCl_2$, and 0.01M phosphate, pH 7.5 (hereinafter "PBS"), containing 10 µg/ml nonradioactive thymidine. Next, the cells were centrifuged at $600 \times g$ and then frozen in an ethanol-dry ice bath.

After thawing, the cell pellet (about 0.7 ml) was resuspended in 9 volumes of lysing solution comprising 0.25% (w/v) Triton X-100, 10 mM EDTA, 10 mM Tris-HCl, pH 7.9. Next, the cell suspension was transferred to a Dounce homogenizer and incubated at room temperature for 20–30 min with gentle mixing.

Then, the cell suspension was transferred to a glass centrifuge tube and NaCl was added to a final concentration of 0.2M. Next, the tube was inverted several times and the solution was immediately centrifuged at $1000 \times g$ at 4° C. for 10 min.

The resulting supernatant was decanted into a glass tube and deproteinized by incubating with 100 µg/ml proteinase K (E. M. Science) in buffer solution comprising 10 mM Tris-HCl, pH 7.5, 1.0 mM EDTA (hereinafter "TE buffer") for 1 hr at 37° C. Then, 1 volume of 90% (v/v) redistilled phenol was added, the solution was mixed by inversion, centrifuged at $20,000 \times g$, and the aqueous phase, i.e., top phase, was transferred to a polyallomer centrifuge tube. Solid sodium acetate was then added to a concentration of 4.0% (w/v), the nucleic acids were precipitated with 2 volumes of ice cold ethanol and incubated overnight at $-20°$ C. Thereafter, the precipitate was collected by centrifugation at 6,000 rpm at 4° C. in a Spinco SW25 rotor, dissolved in 2.0 ml TE buffer, and dialyzed at 4° C. against TE buffer.

The resulting DNA solution was then transferred to a polyallomer centrifuge tube and CsCl in TE buffer was added to 57% (w/w) ($\rho = 1.715$ g/cm$^2$). Next, the DNA was centrifuged for 46 hr at 22.5° C. at 44,000 rpm in a Spinco No. 50 Ti rotor. Then, 12 drop fractions were collected from the bottom of the polyallomer tube and aliquots of 4.0 µl were counted in a liquid scintillation spectrometer to locate the PRV DNA containing fractions ($\rho =$ about 1.727 g/cm$^2$). When a total of 25 fractions were collected, generally fractions 13–15 contained the PRV DNA.

The PRV DNA containing fractions were then pooled and dialyzed against several changes of TE buffer at 4° C. for about 24 hr. The concentrations of DNA was determined fluorometrically. The PRV(BUK-7) DNA yield was about 50 µg from $10^8$ cells.

The identity of the PRV(BUK-7) DNA was verified by the pattern of restriction nuclease-digested PRV(BUK-7) DNA fragments obtained after electrophoresis at 4° C. in a submarine gel apparatus (Bethesda Research Laboratories, Inc.) as described below.

The resulting PRV(BUK-7) DNA was cleaved with BamHI, BglII, and KpnI restriction nucleases under the reaction conditions recommended by the manufacturer (New England BioLabs, Inc.). Next, 1/10 volume of a solution comprising 0.4% (w/v) bromophenol blue, 125 mM EDTA, and 50% (v/v) glycerol was added to terminate the reaction, followed by heating at 65° C for 10 min. Twenty µl aliquots of each sample was applied into the sample wells of the agarose gel, and electrophoresis was carried out as described below.

Figure 2:
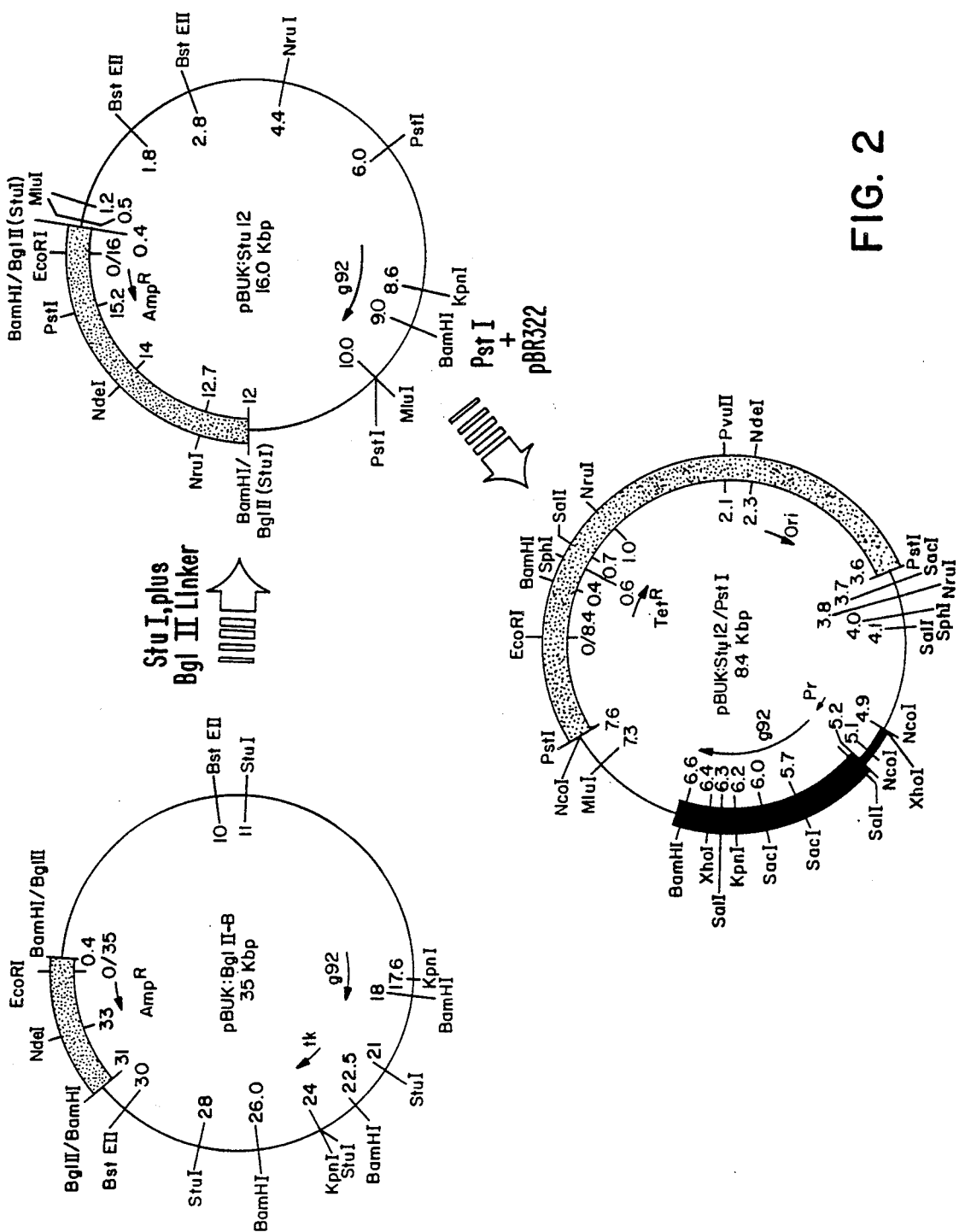
FIG. 2 schematically illustrates, by example, the derivation of pBUK:BglII-B, pBUK:Stu12, pBUK:Stu12/PstI. pBUK:BglII-B was constructed by cloning the 31.6 Kbp BglII fragment of PRV(BUK-7) (see.

Electrophoresis of restriction nuclease fragments was carried out on 0.6% (w/v) agarose slab gels (see: Kit, S., Qavi, H., Dubbs, D. R., and Otsuka, H., *J. Med. Virol.* 12:25–36 (1983)) in electrophoresis buffer comprising 30 mM $NaH_2PO_4$, 1.0 mM EDTA, 40 mM Tris HCl, pH 8.1 (hereinafter "electrophoresis buffer") at 45 volts, 4° C. for about 16 hr. After electrophoresis, DNA fragments were stained by soaking the gel in electrophoresis buffer containing 0.5 µg/ml ethidium bromide, visualized over a long-wave UV illuminator, and photographed. The restriction nuclease patterns were similar to those previously described for PRV DNA (see: Kit, S., Kit, M., and Pirtle, E. C., *Am. J. Vet. Res* 46:1359–1367 (1985) and Lomniczi, B., Blankenship, M. L., and Ben-Porat, T., *J. Virol.* 49:970–979 (1984)). Restriction nuclease maps illustrating the location of BglII, BamHI and KpnI fragments of the PRV(BUK-5) and PRV(BUK-7) genome are shown in FIG. 2 of U.S. Pat. No. 4,514,497. These fragments map at essentially the same locations as do the corresponding DNA fragments of PRV(Kaplan) shown in FIG. 1. PRV(BUK-5) or PRV(BUK-7) could be employed interchangeably in the present invention. The sizes of the BglII, BamHI and KpnI fragments are shown in Table 1 below.

PRV(BUK-7) DNA prepared in this manner had an infectivity of about 100 PFU/µg DNA in the standard transfection assay (see: Graham, F. L. and Van der Eb, A. J., *Virol.* 52:456–467 (1973)).

TABLE 1

| SIZE OF BamHI, KpnI AND BglII Restriction Fragments OF PRV (BUK-5) AND PRV (BUK-7) | | | | | |
|---|---|---|---|---|---|
| BamHI fragment | Kbp | KpnI fragment | Kbp | BglII fragment | Kbp |
| 1 | 30.3 | A | 29.0 | A | 50.8 |
| 2 | 17.8 | B | 21.4 | B | 31.6 |
| 3 | 16.7 | C | 14.5 | C | 28.5 |
| 4 | 9.8 | D | 13.0 | D/E | 19.7 |
| 5 | 8.2 | E | 10.4 | F | 12.3 |
| 5 | 8.2 | F | 9.4 | — | — |
| 5 | 7.5 | G | 8.6 | — | — |
| 6 | 7.5 | H | 8.6 | — | — |
| 7 | 6.7 | I | 4.4 | — | — |
| 8 | 5.1 | $J_L$ | 6.3 | — | — |
| 8 | 5.1 | $J_S$ | 5.9 | — | — |
| 8 | 5.5 | K | 5.9 | — | — |
| 9 | 4.3 | K | 5.9 | — | — |
| 10 | 3.8 | L | 1.7 | — | — |
| 11 | 3.5 | M | 0.7 | — | — |
| 13 | 1.7 | M | 0.7 | — | — |

TABLE 1-continued

SIZE OF BamHI, KpnI AND BglII Restriction Fragments
OF PRV (BUK-5) AND PRV (BUK-7)

| BamHI fragment | Kbp | KpnI fragment | Kbp | BglII fragment | Kbp |
|---|---|---|---|---|---|
| 14 | 1.4 | N | 0.5 | — | — |
| 14 | 1.4 | — | — | — | — |
| 15 | 1.0 | — | — | — | — |
| 16 | 0.8 | — | — | — | — |
| TOTAL: | 146.3 | TOTAL: | 146.9 | TOTAL: | 142.9 |

| Fragments generated by inversion of L segment: | Fragments generated by inversion of L segment: | Fragment E produced by inversion of S segment |
|---|---|---|
| BamHI − Z = 3.2 Kbp | KpnI − X = 1.9 | |
| BamHI − 10B″ = 3.8 Kb | KnI − D + H = 21.6 | |

B. Construction of pBB-11

The 3.5 Kbp BamHI-11 fragment of PRV(BUK-7) was cloned into the single BamHI site of pBR322 as described in U.S. Pat. 4,514,497 as follows (see: FIG. 1 and FIG. 3):

4.0 µg DNA from PRV(BUK-7) was dissolved in cutting buffer comprising 150 mM NaCl, 6.0 mM Tris-HCl, pH 7.9, 6.0 mM $MgCl_2$ and 100 µg/ml bovine serum albumin (hereinafter "BSA") (hereinafter "BamHI cutting buffer"). The DNA was then digested at 37° C. for 1 hr with 40 units of BamHI. The reaction was terminated by adding an equal volume of 90% (v/v) redistilled phenol, mixing, and centrifuging for phase separation. After dialysis of the aqueous phase against 0.1×TE buffer sodium acetate was added to 0.1M followed by the addition of 2 volumes of ethanol, and the DNA precipitate was collected by centrifugation and dissolved in 0.1×TE buffer.

The restriction nuclease fragments were then combined with pBR322 which had been cleaved with BamHI and dephosphorylated in the following manner:

4.0 µg of BamHI-cleaved PRV(BUK-7) DNA was mixed with 0.2 µg of BamHI-digested, dephosphorylated pBR322 DNA (New England BioLabs Inc.), in 0.05 ml of ligation buffer solution comprising 50 mM Tris-HCl pH 7.8, 10 mM $MgCl_2$, 20 mM dithiothreitol, 1.0 mM, ATP, 50 µg/ml BSA (hereinafter "ligation buffer"), and containing 1000 units of phage T4 DNA ligase (New England BioLabs, Inc.), and incubated overnight at 4° C. The reaction was terminated by adding EDTA to 20 mM and heating at 65° C. for 30 min.

The recombinant plasmid DNA was diluted in TE buffer and used to transform E. coli K12 RR1 bacteria as described below (see: Bolivar, F. Rodriguez, R. L., Greene, P. J., Betlach, M. C., Heyneker, H. L., Boyer, H. W., Crosa, J. H., and Falkow, S., *Gene* 2:95–113 (1977)).

Bacteria were prepared for transformation using $CaCl_2$ (see: Mandel, M. and Higa, A., *J. Mol. Biol.* 53:159–162 (1970)). Specifically, an overnight culture at a density of 2.0 ($A_{600}$) of E. coli K12 RR1 was used to inoculate 200 ml of broth comprising 1.0% (w/v) bactotryptone, 0.5% (w/v) yeast extract, and 0.5% (w/v) NaCl (hereinafter "ML broth"), at a bacterial density of 0.02 ($A_{600}$). The bacteria were incubated for about 2 hr until a density of about 0.5 ($A_{600}$) was achieved. The bacteria were then pelleted by centrifugation and resuspended in ¼ volume of cold 50 mM $CaCl_2$. After a 5-min incubation on ice, the bacteria were again pelleted and resuspended in 1/40 the volume of ice cold 50 mM $CaCl_2$.

Next, 1/10 ml of the recombinant plasmid DNA, about 10–100 ng, in TE buffer was added to 0.2 ml of the $CaCl_2$-treated bacteria. The mixture was kept at 4° C. for 30 min. Then, the temperature was raised to 37° C. for 5 min and 0.3 ml of ML broth was added. Thereafter, incubation was continued for 45 min at 37° C. with gentle shaking. Samples were plated on trypticase soy agar plates (BBL Microbiology Systems) supplemented with 30 µg/ml ampicillin.

Rapid screening of the resulting clones for the desired recombinant plasmid DNA was conducted as follows:

An overnight culture of bacteria containing recombinant plasmid DNA was inoculated into 5.0 ml of ML broth containing 30 µg/ml ampicillin and incubated at 37° C. to a density of about 1.5 ($A_{600}$). One ml of this bacterial culture was then transferred to a 1.5 ml Eppendorf polypropylene tube and centrifuged in an Eppendorf centrifuge for about 1 min at room temperature to pellet the bacteria. Next, the bacteria was resuspended in 0.1 ml of a solution comprising 2.0 mg/ml egg lysozyme, 50 mM glucose, 10 mM cyclohexanediamine tetraacetate (hereinafter "CDTA"), and 25 mM Tris-HCl buffer, pH 8.0 (hereinafter "lysozyme solution No. 1"), and then incubated for 30 min at 4° C. Next, 0.2 ml of 0.2N NaOH plus 1.0% (w/v) sodium dodecylsulfate was added to the bacterial suspension and the tube was vortexed and kept at 4° C. for 5 min. Thereafter, 0.15 ml of 3.0M sodium acetate, pH 4.8, was added, and the tube was gently inverted, during which time a "clot" of DNA formed. The DNA was kept at 4° C for 1 hr to allow chromosomal DNA, protein, and high molecular weight RNA to precipitate. Next, the precipitate was centrifuged in an Eppendorf centrifuge for 5 min at room temperature and the clear supernatant fluid, approximately 0.4 ml, containing recombinant plasmid DNA was transferred to a second Eppendorf centrifuge tube. Then, 2½ volumes of ethanol (approximately 1.0 ml) were added to the second tube which was placed at −20° C. for 30 min. The precipitated recombinant plasmid DNA was collected by centrifugation for 2 min at room temperature in an Eppendorf centrifuge. Then, the recombinant plasmid DNA was dissolved in 0.1 ml of 0.1M sodium acetate. 0.05M Tris-HCl, pH 8.0, reprecipitated with ethanol, collected by again centrifuging, and finally dissolved in 50 µl of water.

Then, a 10 µl aliquot of plasmid DNA was diluted in BamHI cutting buffer and 2.0 units of BamHI were added. Following a digestion period of 60 min at 37° C. the sample was mixed with 1/10 volume of a solution comprising 0.4% (w/v) bromophenol blue, 125 mM EDTA, and 50% (v/v) glycerol, and about 20 µl was applied to a 0.6% (w/v) agarose slab gel for electrophoretic analysis as described above. This analysis revealed whether the recombinant plasmid contained a BamHI insert and, if so, the size, in Kbp, of the insert (see: Birnboim, H. C. and Doly, J., *Nucl. Acids Res.* 7:1513–1523 (1973)).

For large-scale preparation of recombinant plasmid DNA, 200 times the amount of plasmid-transformed bacteria were processed as compared with the bacteria used to produce recombinant plasmid DNA for the rapid screening procedure described above, except that after the first ethanol precipitation, the sample was treated, at 37° C. for 30 min, with 0.5 mg of pancreatic RNase A (Worthington Biochemicals) from a stock solution comprising 1.0 mg/ml RNase A in 5.0 mM Tris-HCl, pH 8.0 which had been heated at 100° C. for 10 min. The treatment was followed by the addition of 500 μg of proteinase K (E. M. Science) in TE buffer at 37° C. for 30 min. Subsequently, an equal volume of phenol was added, the sample was vortexed and centrifuged as described above to separate the phases. The aqueous phase was then removed, precipitated with ethanol, and collected by centrifugation as described above. The precipitate was then dissolved in 0.2 ml of TE buffer and layered on a 10.4 ml linear 10–40% (w/v) sucrose gradient in 50 mM NaCl, 10 mM Tris-HCl, pH 7.5, 1.0 mM EDTA, and was then centrifuged at 4° C. for 20 hr at 24,000 rpm in a Spinco SW41 rotor. Fifteen drop fractions were collected from the bottom of polyallomer centrifuge tubes into wells of plastic trays. A total of 35 fractions was obtained. Five μl aliquots were then screened by employing agarose gel electrophoresis as described above. Fractions containing recombinant plasmid DNA were pooled, dialyzed against 0.1×TE buffer, and stored at 4° C. for further studies.

Using these procedures, a plasmid about 7.9 Kbp in size comprising the approximately 3.5 Kbp BamHI-11 fragment of PRV(BUK-7) cloned into the single BamHI site of pBR322 was isolated and designated pBB-11 (see: FIG. 3).

C. Cloning of pBUK:BglII-B

The 31.6 Kbp BglII-B fragment of PRV(BUK-7) was cloned into the BamHI site of pBR322 as follows (see: FIGS. 1 and 2):

4.0 μg of PRV(BUK-7) DNA was dissolved in 100 μl of a buffer comprising 100 mM NaCl, 10 mM Tris-HCl, pH 7.4, 10 mM MgCl$_2$, 10 mM 2-mercaptoethanol, 100 μg/ml BSA (hereinafter "BglII cutting buffer") and digested with 32 units of BglII (New England BioLabs, Inc.) for 1 hr at 37° C. The reaction was terminated by adding an equal volume of 90% (v/v) redistilled phenol, mixing, and centrifuging for phase separation. After dialysis of the aqueous phase against 0.1×TE buffer, sodium acetate was added to 0.1M followed by the addition of 2 volumes of ethanol, and the DNA precipitate was stored at −20° C. overnight. The DNA precipitate was collected by centrifugation and redissolved in 0.1×TE buffer.

The restriction nuclease fragments were then combined with BamHI-digested, dephosphorylated pBR322 in the following manner:

4.0 μg of BglII-digested PRV(BUK-7) DNA was mixed with 0.2 μg of BamHI-digested, dephosphorylated pBR322 DNA (New England BioLabs, Inc.) in 0.05 ml of ligation buffer containing 1000 units of T4 DNA ligase (New England BioLabs, Inc.), and incubated overnight at 4° C. The reaction was terminated by adding EDTA to 20 mM and heating at 65° C. for 10 min. The recombinant DNA plasmid was used to transform *E. coli* K12 strain RR1, as described above, and the resulting colonies were screened by the rapid plasmid screening procedure, as described above.

Using these procedures, a plasmid, about 35 Kbp in size, comprising the approximately 31.6 Kbp BglII-B fragment of PRV(BUK-7) cloned into the BamHI site of pBR322 was isolated and designated pBUK:BglII-B (see: FIG. 2).

D. Subcloning pBUK-BglII-B and Construction of pBUK:Stu12

The StuI fragment from pBUK:BglII-B, which maps at about 11 to 21 map units, was transferred to the single BamHI site of pBR322 as follows (see: FIG. 2):

1.0 μg of pBUK:BglII-B was dissolved in 100 μl of a buffer comprising 100 mM NaCl, 10 mM Tris-HCl pH 8.0, 10 mM MgCl$_2$, 6.0 mM 2-mercaptoethanol, 100 μg/ml BSA (hereinafter "StuI cutting buffer"). The DNA was digested by the addition of 10 units of StuI (New England BioLabs, Inc.) and incubated at 37° C. for 1 hr. The reaction was terminated by the addition of CDTA to 20 mM and sodium acetate to 0.2 M, followed by heating at 65° C. for 30 min. The DNA was precipitated with ethanol and collected by centrifugation as described above.

The StuI-digested pBUK:BglII-B was dissolved in 25 μl of ligation buffer containing 1.0 μg of phosphorylated BglII linker (New England BioLabs, Inc.) and 1000 units of T4 DNA ligase. After overnight incubation at 4° C. the reaction was terminated by adding EDTA to 20 mM and heating at 65° C. for 10 min. The StuI-digested pBUK:BglII-B, now possessing concatenated BglII linkers at the former StuI termini, was separated from the unligated BglII linkers by layering the reaction mixture on a 10–40% (w/v) sucrose gradient in 50 mM NaCl, 10 mM Tris-HCl, pH 7.5, 1.0 mM EDTA, and centrifuging for 8 hr at 40,000 rpm at 4° C. in an SW41 Spinco rotor. Fractions were collected and the DNA located by analyzing aliquots on agarose gel electrophoresis as described above. The linkers remained at the top of the gradient, whereas the plasmid DNA sedimented to the middle of the gradient. After adding sodium acetate to 0.1M and 2.0 μg of carrier yeast tRNA to each fraction, the plasmid DNA was precipitated with ethanol, collected by centrifugation, dissolved in 50 μl of BglII cutting buffer, and then digested with 8 units of BglII (New England Biolabs, Inc.) at 37° C. for 1 hr in order to create BglII cohesive ends. The reaction was terminated, the DNA was precipitated with ethanol, and collected by centrifugation, as described above.

The StuI-digested pBUK:BglII-B, now containing BglII cohesive ends on the StuI fragments, was cloned into the BamHI site of pBR322 by first dissolving the DNA in 50 μl of ligation buffer. Then, 0.1 μg of BamHI-digested, dephosphorylated pBR322 was added and the mixture was ligated with 1000 units of T4 DNA ligase, as described above. After termination of the ligation reaction, *E. coli* K12 RR1 was transformed with the hybrid plasmids and the resulting colonies were screened for recombinants, as described above.

Using these procedures, a plasmid about 16 Kbp in size comprising the approximately 12 Kbp StuI fragment derived from pBUK:BglII-B cloned in the single BamHI site of pBR322 was isolated and designated pBUK:Stu12 (see: FIG. 2).

E. Construction of pBUK:Stu12/PstI

The 4.0 Kbp PstI fragment from pBUK:Stu12 containing the PRV g92 gene was transferred to the PstI site of pBR322 as follows (see: FIG. 2):

2.0 μg of pBUK:Stu12 was dissolved in 100 μl of a buffer comprising 100 mM NaCl, 10 mM Tris-HCl, pH 7.5, 10 mM MgCl$_2$, 100 μg/ml BSA (hereinafter "PstI cutting buffer") and digested with 10 units of PstI (New England BioLabs, Inc.) for 1 hr at 37° C. The reaction was terminated by the addition of CDTA to 20 mM and heating at 65° C. for 30 min. Then, sodium acetate was added to 0.1M and the DNA was ethanol precipitated and collected by centrifugation. The 4 Kbp PstI fragment of pBUK:Stu12 was cloned into the PstI site of pBR322 by dissolving the plasmid DNA in 50 μl of ligation buffer containing 0.2 μg of PstI-digested and dephosphorylated pBR322 (New England BioLabs, Inc.) and 1000 units of T4 DNA ligase, then incubating at 4° C. overnight. The reaction was terminated by the addition of EDTA to 20 mM and heating at 65° C. for 10 min. The recombinant DNA was introduced into *E. coli* K12 RR1 by transformation, and colonies were screened by the rapid plasmid screening procedure, as described above, for a plasmid about 8.4 Kbp in size and containing the 4.0 Kbp PstI fragment from pBUK:Stu12 cloned into the PstI site of pBR322. In this manner, a representative recombinant plasmid was isolated and designated pBUK:Stu12/PstI (see: FIG. 2).

F. Construction of pBB-11(g92Xho)

The PRV g92 gene promoter was transferred to the PRV tk gene by mobilizing a 1.4 Kbp XhoI fragment from pBUK:Stu12/PstI and inserting it into the single XhoI site of plasmid pBB-11 as follows (see: FIG. 3):

4.0 μg of pBUK:Stu12/PstI was dissolved in 200 μl of a buffer comprising 150 mM NaCl, 6.0 mM Tris-HCl, pH 7.9, 6.0 mM MgCl$_2$, 6.0 mM 2-mercaptoethanol, 100 μg/ml BSA (hereinafter "XhoI cutting buffer") and digested with 20 units of XhoI enzyme (New England Biolabs, Inc.) at 37° C. for 2 hr. The reaction was terminated by adding CDTA to 20 mM and sodium acetate to 0.3M, followed by heating at 65° C. for 30 min. The DNA was precipitated by adding 2 volumes of ethanol incubating overnight at −20° C. and collecting by centrifugation.

In addition, 2.0 μg of pBB-11 was dissolved in 200 μl of XhoI cutting buffer and digested with 20 units of XhoI at 37° C. for 2 hr. The reaction was terminated and the DNA collected by centrifugation as described above.

In order to reduce the frequency of recircularization of pBB-11 cleaved with XhoI, and thereby promote the derivation of recombinants, pBB-II cleaved with XhoI was dephosphorylated as follows.

The pBB 11 cleaved with XhoI was dissolved in 90 μl of a buffer comprising 50 mM Tris-HCl, pH 8.0, 50 mM NaCl (hereinafter "alkaline phosphatase buffer") and digested with 0.22 units of bacterial alkaline phosphatase (International Biotechnolgies) at 65° C. for 1 hr. Then proteinase K (E.M. Science) was added to 100 μg/ml and the incubation continued at 37° C. for 30 min. The reaction was terminated by adding an equal volume of 90% (v/v) redistilled phenol, vortexing, and centrifuging for phase separation. The aqueous phase was extracted with ether, brought to 0.3M sodium acetate, and precipitated by adding 2 volume of ethanol. After overnight incubation at −20° C., the DNA was collected by centrifugation and air dried.

Finally, the 1.4 Kbp XhoI fragment from pBUK:Stu12/PstI was transferred into the single XhoI site of pBB-11 by ligating the XhoI fragments of pBUK:Stu12/PstI with the XhoI cleaved and dephosphorylated pBB-11 in 50 μl of ligation buffer and 1000 units of T4 DNA ligase (New England Biolabs Inc.). The reaction was carried out at 4° C. overnight, then terminated by adding EDTA to 20 mM followed by heating at 65° C. for 10 min.

The recombinant plasmid DNA was diluted in TE buffer and used to transform *E. coli* K12 RR1 bacteria as described above.

Rapid screening of the resulting colonies for the desired recombinant plasmid DNA was conducted as described above.

Then a 10 μl aliquot of plasmid DNA was diluted in XhoI cutting buffer and 2.0 units of XhoI were added. Following a digestion period of 60 min at 37° C. the sample was mixed with 1/10 volume of a solution comprising 0.4% (w/v) bromophenol blue, 125 mM EDTA, and 50% (v/v) glycerol, and about 20 μl was applied to a 0.6% (w/v) agarose slab gel for electrophoretic analysis as described above. This analysis revealed whether the recombinant plasmid contained a XhoI insert and, if so, the size, in Kbp, of the insert (see: Birnboim, H. C. and Doly, J., *Nucl. Acids Res.* 7:1513 1523 (1973)).

Using these procedures, a plasmid about 9.3 Kbp in size comprising the approximately 1.4 Kbp XhoI fragment of pBUK:Stu12/PstI cloned in the single XhoI site of pBB-11 was isolated and designated pBB-11(g92Xho) (see: FIG. 3).

G. Construction of pBB-11(g92Xho)dl Nco-Mlu

A plasmid containing the PRV g92 promoter followed by convenient unique restriction nuclease recognition sites after the initiation codon of the g92 gene, all inserted into the PRV tk gene was obtained from pBB-11(g92Xho). That is, the PRV g92 gene sequences in pBB-11(g92Xho) which were distal to the NcoI site (the initiation codon is contained within the NcoI site) were deleted and replaced with an oligonucleotide adaptor with unique restriction sites as follows (see: FIG. 4):

2.0 μg of pBB-11(g92Xho) was dissolved in 200 μl of a buffer comprising 150 mM NaCl, 6.0 mM Tris-HCl, pH 7.9, 6.0 mM MgCl$_2$, 100 g/ml BSA (hereinafter "NcoI cutting buffer") and digested with 20 units of NcoI enzyme (New England Biolabs, Inc.) at 37° C. for 2 hr. The reaction was terminated by adding CDTA to 20 mM and sodium acetate to 0.3M, followed by heating at 65° C. for 30 min. The DNA was ethanol precipitated and collected by centrifugation as described above.

The following oligonucleotides were synthesized by phosphoramidite chemistry on a Systec automated DNA synthesizer as described by the manufacturer.

5'-CATGGCAGATCTAGA-3' and
5'-CGCGTCTAGATCTGC-3'

The oligonucleotides were phosphorylated by dissolving 1.0 μg of each in ligation buffer with 2 units of polynucleotide kinase (New England Biolabs, Inc.) and incubating at 37° C. for 1 hr. The phosphorylated oligonucleotides were annealed at 37° C. for 30 min, then at 22° C. for 30 min to generate a duplex with the following sequence and restriction enzyme sites internally, and NcoI or MluI cohesive ends.

5'-pCATGGCAGATCTAGA-3'
3'-CGTCTAGATCTGCGCp-5'

(NcoI-BglII-XbaI-MluI oligonucleotide)

The duplex oligonucleotide adaptor was ligated to the NcoI cohesive ends of the NcoI cleaved pBB-11(g92Xho) by adding the phosphorylated oligonucleotides and the NcoI cleaved pBB-11(g92Xho) into 50 μl final volume of ligation buffer and 1000 units of T4

DNA ligase and incubating at 22° C. for 5 hr then at 4° C. overnight. The reaction was terminated by adding EDTA to 20 mM and heating at 65° C. for 30 min.

The NcoI cleaved pBB-11(g92Xho) with attached adaptors was separated from free oligonucleotides by layering the sample on a 10–40% (w/v) sucrose gradient in 50 mM NaCl, 1 mM Tris-HCl, pH 7.5, 1.0 mM EDTA, in a polyallomer tube and centrifuging in a SW41 Spinco rotor at 40,000 rpm, 4° C. for 8 hr. Fractions were collected from the bottom of the tube and the plasmid localized by analyzing aliquots on agarose gels after electrophoresis as described above. Fractions containing the plasmid DNA were brought to 0.3M sodium acetate, 2.0 μg per fraction of yeast carrier tRNA was added, and the DNA precipitated by adding 2 volumes of ethanol and incubating overnight at −20° C. The DNA was collected by centrifugation and air dried as described above.

The NcoI cleaved pBB-11(g92Xho) with adaptors attached to the NcoI end was then dissolved in 100 μl of a buffer comprising 50 mM NaCl, 10 mM Tris-HCl, pH 7.5, 7 mM MgCl$_2$, 6.0 mM 2-mercaptoethanol, and 100 μg/ml BSA (hereinafter "MluI cutting buffer") and digested with 10 units of MluI enzyme (New England Biolabs, Inc.) at 37° C. for 2 hr. The reaction was terminated by adding CDTA to 20 mM and sodium acetate to 0.3M, then heating at 65° C. for 30 min. The DNA was ethanol precipitated and collected as described above. Cutting the NcoI cleaved pBB-11(g92Xho) with attached adaptors with MluI converted the polyadaptor ends to unit length, and cleaving the MluI site in pBB-11 distal to the inserted XhoI fragment, removed all g92 gene sequences distal to the NcoI site, and approximately a 10 bp fragment of the PRV tk gene between the XhoI and MluI site of pBB-11.

The NcoI and MluI cleaved pBB-11(g92Xho) with an NcoI-BglII-XbaI-MluI adaptor attached to the NcoI end of the cleaved plasmid was recircularized by dissolving the DNA in 50 μl of ligation buffer and 1000 units of T4 DNA ligase and ligating at 4° C. overnight. The reaction was terminated and bacteria transformed as described above.

The recombinants were screened by the rapid plasmid screening procedure as described above, for a plasmid with a 1.2 Kbp deletion. In this manner, a 8.1 Kbp plasmid was isolated and designated pBB-11(g92Xho)dl Nco-Mlu (see: FIG. 4). This plasmid contained a 10 bp deletion in pBB-11 between the single XhoI and MluI sites into which was cloned a 0.2 Kbp XhoI-NcoI fragment containing the PRV g92 gene promoter followed by a NcoI-BglII-XbaI-MluI adaptor..

H. Construction of pBB-11(βGalex)

The lacZ gene of *E. coli* was inserted distal to the PRV g92 gene promoter in a manner such that the initiation codon of the PRV g92 gene preceded and was in phase with the 8th amino acid of the lacZ gene. With this construction a functional β-galactosidase enzyme (minus the non-essential first 7 amino acids) would be produced under an environment where the PRV g92 gene promoter was active. The lacZ gene was obtained as a gift from Malcolm J. Casadaban as a 3 kb PstI fragment inserted into the PstI site of pBR322, which had been designated pMCI871 (see: *Methods in Enzymology*, 100:293 (1983)). This construction was carried out as follows (see: FIG. 4):

2.0 μg of pMCI871 was dissolved in BamHI cutting buffer and digested with 20 units of BamHI (New England Biolabs, Inc.) at 37° C. for 2 hr. The reaction was terminated by adding CDTA to 0.1M and sodium acetate to 0.3M, and heating at 65° C. for 30 min. The DNA was ethanol precipitated and collected by centrifugation as described above. 2.0 μg of pBB-11(g92Xho)dl Nco-Mlu was dissolved in BglII cutting buffer and digested with 8 units of BglII (New England Biolabs, Inc.) at 37° C. for 2 hr. The reaction was terminated and the DNA collected as described above.

In order to reduce recircularization of the plasmid vector, the BglII cleaved pBB-11(g92Xho)dl Nco-Mlu was dissolve in 100 μl of alkaline phosphatase buffer containing 0.22 units of bacterial alkaline phosphatase, then incubated at 65° C. for 1 hr. Proteinase K (E.M. Science) was added to 100 μg/ml and the reaction continued at 37° C. for 30 min. The reaction was terminated by adding an equal volume of 90% (v/v) redistilled phenol, vortexing, and centrifuging for phase separation. The aqueous phase was extracted several times with excess ether, brought to 0.3M sodium acetate, and the DNA was ethanol precipitated and collected by centrifugation.

The BamHI fragment from pMCI871 was ligated into the BglII site of pBB-11(g92Xho)dl Nco-Mlu by dissolving the BamHI cleaved pMCI871 and the BglII cleaved and dephosphorylated pBB-11(g92Xho)dl Nco-Mlu in 50 μl of ligation buffer containing 1000 units of T4 DNA ligase, then incubating at 4° C. overnight. The reaction was terminated, and bacteria transformed as described above.

Using these procedures, a 11.1 Kbp plasmid comprising the approximately 3 Kbp BamHI fragment from pMCI871 cloned into the BglII site of pBB-11(g92Xho)dl Nco-Mlu was isolated and designated pBB-11(β-Galex) (see: FIG. 4).

I. Construction of PRV(BUK-β-Gal), i.e., a PRV(BUK) recombinant expressing the lacZ gene In order to obtain, by homologous recombination, a PRV insertion mutant in the tk gene, it was necessary to start with the intact DNA of a tk+ PRV and a hybrid plasmid containing an insertion in the coding region of the tk gene. The progeny virus obtained following this type of cross mainly comprise parental tk PRV. Thus, in order to enrich for the tk− PRV recombinants in the harvests, selective media containing IUdR was employed, since IUdR inhibits tk+ PRV replication and favors the outgrowth of tk− PRV.

The hybrid plasmid chosen for the construction of a tk− insertion mutant of PRV was pBB-11(β-Galex). However, other hybrid plasmids containing larger or smaller flanking sequences adjacent to the coding sequence of the PRV tk gene or larger or smaller insertions in the same or other portions of the tk gene or other non-essential PRV DNA sequence, could be employed to create "insertion" mutations, without departing from the scope and spirit of this invention.

The tk+ PRV DNA chosen for the recombination step was PRV(BUK-5AR1). Since PRV(BUK-5AR1) was derived from PRV(BUK), a known vaccine strain PRV(BUK-5AR1) was the preferred virus to other tk+ PRV field strains for the construction of the insertion mutant. However, as described above, other strains would be equally suitable without departing from the scope and spirit of this invention.

In order to transfer the lacZ gene into the PRV virus, an homologous recombination event occurs intracellularly following transfection of DNA by the calcium phosphate precipitate method (see Graham. F. L. and Van der Eb, A. J., *Virol.* 52:456–467 (1973)). The construction of the tk− PRV with an insertion of the lacZ gene in the PRV tk gene, and under the control of the PRV g92 gene promoter was carried out as follows (see: FIG. 5):

Rab-9 cells were seeded in 60 mm Petri dishes ($0.2 \times 10^6$ cells/dish) and incubated at 37° C. for 48 hr. Then, the following sterile solutions were added to a test tube in sequential order:

(1) 0.02 ml of a 50 μg/ml solution of the tk+ PRV(BUK-5A R1) (see: U.S. Pat. No. 4,514,497) in TE buffer:

(2) 0.2 ml of a 10 μg/ml solution of BamHI digested plasmid pBB-11(β-Galex). The BamHI digested plasmid was obtained by dissolving 10 μg of pBB-11(β-Galex) in 500 μl of BamHI cutting buffer and then digesting the plasmid for 1 hr with 100 units of BamHI, and thereafter incubating the reaction mixture for 1 hr at 37° C. with proteinase K (E.M. Science) at 100 μg/ml. The reaction mixture was vortexed with an equal volume of phenol, centrifuged for phase separation, extracted with ether and dialyzed against $0.1 \times TE$ buffer:

(3) 0.65 ml $H_2O$;

(4) 1.0 ml of 20 μg/ml solution of salmon sperm DNA in $2 \times a$ HEPES buffer solution comprising 8.0 g/l NaCl, 0.37 g/l KCl, 0.125 g/l $Na_2HPO_4.2H_2O$, 1.0 g/l glucose, 5.0 g/l HEPES, pH 7.05; and (5) 0.13 ml of 2.0 M $CaCl_2$.

The resulting solution was mixed by inversion and kept at room temperature for 30 min while a DNA-calcium precipitate formed. Then, 0.5 ml of the suspension containing the resulting calcium phosphate DNA precipitate was added directly to 5.0 ml of growth medium and plated on Rab-9 cells which had been seeded in 60 mm Petri dishes 48 hr earlier. The cells were incubated at 37° C. for 5 hr. Then, the media was aspirated, and the monolayer rinsed with 5.0 ml of fresh growth media, followed by the addition of 1.0 ml of a solution of a $1 \times$ HEPES buffer solution plus 15% (v/v) glycerol. After a 3-min incubation at room temperature, the solution was aspirated, the monolayer rinsed with media again, and fresh growth media added. The culture was incubated at 34.5° C. for 2 days until extensive cytopathic effects occurred. Virus harvests were made as described above and stored at −80° C. The virus harvest was then titrated in Rab-9 cells under agar overlay.

The virus harvest from the co-transfection was thawed, sonicated, and diluted in growth media supplemented with 100 μg/ml 5'-iododeoxyuridine (hereinafter "IdUrd"). In order to enrich for tk+ PRV recombinants, the harvested virus was diluted to give an input multiplicity of 0.01 PFU/cell and passaged in subconfluent monolayer cultures of Rab(BU) cells in 8-oz prescription bottles in growth medium supplemented with 100 μg/ml IdUrd. After a 1-hr absorption at 37° C., the infected monolayer cultures were washed three times with 8.0 g NaCl, 0.4 g KCl, 0.1 g glucose and 0.02 g phenol red per liter of water (hereinafter "GKN"). Then, growth medium containing 100 μg/ml IdUrd was added. incubation was continued at 34.5° C. for 48 hr, and virus harvests were made. The harvest of the selective passage was titrated in Rab-9 cells, except that after 3 days of incubation, neutral red was replaced with an equal volume of a second agar overlay containing 600 μg/ml dye X-Gal (Boehringer-Mannheim) instead. After an additional 24 hr incubation at 34.5° C. blue plaques were visualized indicating the expression of β-galactosidase. The candidate recombinant viruses were selected at random and resuspended in 0.5 ml of growth medium. The candidate recombinant viruses were propagated in Rab-9 cells, and harvested as described above.

J. Identification of PRV Recombinants With An Insertion of the lacZ Gene Into the PRV tk Gene Viral DNAs prepared from the candidate recombinant viruses described above were analyzed with restriction nucleases to identify recombinants containing a 3 Kbp insertion of the lacZ gene in the fragment of PRV containing the tk gene. Viral DNA of high purity was prepared. Then, 0.5 μg of viral DNA was dissolved in BamHI cutting buffer and digested with 5 units of BamHI for 1 hr at 37° C. In addition, 0.5 μg of viral DNA was dissolved in a buffer comprising 6.0 mM NaCl, 6.0 mM Tris-HCl, pH 7.5, 6.0 mM dithiothreitol, 100 μg/ml of BSA and digested with 5 units of KpnI (New England Biolabs, Inc.) for 1 hr at 37° C. The reaction was terminated by adding 1/10 volume of a solution comprising 0.4% (w/v) bromophenol blue, 125 mM EDTA and 50% (v/v) glycerol, followed by heating at 65° C. for 10 min. Next, the fragments were separated by electrophoresis on agarose gels as described above.

The ethidium stained gels revealed that in the candidate recombinants, designated PRV(BUK-β-Gal) clones 1, 2 or 3, the KpnI-$J_L$ fragment had been replaced by a fragment 3 Kbp larger, and that the BamHI-11 fragment had been replaced by a fragment, also 3 Kbp larger. These results are consistent with an insertion of a 3 Kbp fragment into the XhoI site of the PRV tk gene, which is in both the KpnI-$J_L$ and BamHI-11 of PRV(BUK-5A) DNA fragments see: U.S. Pat. No. 4,514,497). One of the clones of PRV(BUK-β-Gal), i.e., clone 1 has been deposited at the American Type Culture Collection under ATCC No. VR-2133.

EXAMPLE 2

TK Activity Of PRV Strains

In order to analyze the phenotype of the 3 clones of the PRV tk insertion mutant PRV(BUK-β-Gal) (see: FIG. 5). autoradiography of infected cells was performed as follows:

Rab(BU) cells were seeded (50,000 cells/well) into an 8-well Lab-Tek ™ (Miles Laboratories, Inc.) slide and incubated for 1-2 days at 37° C. until confluent. The cells were infected at about 10 PFU/cell with the virus strains PRV(BUK-5) and PRV(BUK-dl 3) or with the recombinant virus PRV(BUK-β-Gal). After a 1-hr absorption at 37° C., fresh growth media was added. At 3 hr post-infection, the growth media was changed to fresh growth medium with 5.0 μCi $^3$H-dThd/ml 0.1 μg/ml dThd. At 20 hr post-infection, the medium was aspirated and the cells were rinsed with GKN, methanol, and then fixed in methanol for 1 min at room temperature. The wells and gasket were removed from the slide and the cells were washed at 4° C. for 5 min each with 5.0% (w/v) trichloroacetic acid (twice) 70% (v/v) ethanol (3 times), and 100% ethanol (twice). After drying in air, the slides were stained in 2.0% (w/v) acericorcein for 2 min, then destained in ethanol. The slides were dipped in autoradiographic photographic emulsion (Kodak-NTB2) at 40° C. and dried in a horizontal position for 1 hr. Then the slides were placed in a darkened box with drierite and left at room temperature for 20 hr. The slides were developed in Kodak Dektol for 2 min at 16° C., rinsed in water for 10 sec, fixed in Kodak fixer for 5 min, and rinsed in water 2 times, each for 2.5 min.

In all cells infected with PRV(BUK-5), i.e., a tk+ PRV, the nuclei were heavily labeled due to the phosphorylation of $^3$H-dThd by the PRV TK enzyme, and the subsequent incorporation of the $^3$H-dTTP into acid insoluble nuclear DNA. As expected, PRV(BUK-dl 3) and PRV(BUK-β-Gal) produced pronounced cytopathic effects in the infected cells due to virus growth, but the nuclei of the cells infected with these viruses were not labeled because of the absence of a functional TK enzyme with which to phosphorylate the $^3$H-dThd. Thus, these experiments demonstrate that PRV(BUK-β-Gal) is a tk− PRV.

The PRV(BUK-β-Gal) clones were also analyzed by thymidine plaque autoradiography for the presence of tk− PRV (see: Tenser, R. B., Jones, J. C., Ressel, S. J. and Fralish, F. A., *J. Clin. Microbiol.* 17:122–127 (1983)) as follows:

100 mm plastic tissue culture grade Petri dishes were seeded with $1.25 \times 10^6$ Rab(BU) cells in 10 ml of growth medium and incubated at 37° C. in a humidified $CO_2$ incubator until the monolayer was semiconfluent (2 days). Then, the medium was removed by aspiration, and 0.5 ml of thawed and sonicated virus samples in growth medium was added at 200 to 1000 PFU/dish and absorbed to the monolayers at 37° C. for 1 hr. The dishes were overlayed with 10 ml of 0.5% (w/v) methyl cellulose in growth medium and incubated at 37° C. for 2 days. The methyl cellulose overlay was removed by aspiration; then the monolayers were rinsed with GKN followed by the addition of 5.0 ml of growth medium containing 3 μCi of (methyl-$^{14}$C)thymidine (53–59 mCi/mmole) to each dish. At the end of a 6 hr incubation at 37° C. the medium was removed and the monolayers were rinsed with GKN and methanol, and then fixed with methanol for 1 min at room temperature. The monolayers were subsequently washed two times for 5 min each with 5% (w/v) trichloroacetic acid containing 10 g/ml non-radioactive thymidine, three times for 5 min each with 70% (v/v) ethanol, and two times for 5 min each with 90% (v/v) ethanol then two times for 5 min each with 100% ethanol, all at 4° C. The monolayer was dried, and 10 ml of 0.1% (w/v) crystal violet in water was added for 5 min followed by rinsing with tap water and drying at room temperature. The bottoms of the plates were cut out, mounted on cardboard, and placed in a folder with Fuji X-ray film and exposed at −70° C. for 2 days. The film was developed, and the number of dark rim circles representing isotope incorporation by tk+ plaques were counted and compared to the number of total plaques visible on the crystal violet stained monolayers. Only PRV(BUK-5) produced plaques with dark circles indicating the tk+ phenotype. The results confirmed that all three insertion mutant clones of PRV(BUK-β-Gal) have the tk− phenotype.

In addition to the autoradiographic experiments described above, cytosol extracts from PRV-infected cells were assayed for $^3$H-dThd-phosphorylating activity to verify that clones of PRV(BUK-β-Gal) lacked TK-inducing activity (see: U.S. Pat. No. 4,514,497, and Kit, S., Kit, M., and Pirtle, E. C., *Am. J. Vet. Res.* 46:1359–1367 (1985)). The results are shown in Table 2 below:

TABLE 2

THYMIDINE KINASE (TK) ACIVITY OF Rab (BU) CELLS INFECTED FOR 6.5 HR WITH tk+ PRV AND tk− PRV VIRUSES

| PRV strain used to infect Rab (BU) cells | TK activity[a] |
|---|---|
| Mock-infected Rab (BU) | 0.16 |
| PRV (BUK-5) | 7.70 |
| PRV (BUK-β-Gal) - clone 1 | 0.15 |
| PRV (BUK-β-Gal) - clone 2 | 0.15 |
| PRV (BUK-β-Gal) - clone 3 | 0.13 |

[a]picomoles $^3$H-dTMP formed from $^3$H-dThd in 10 min at 38° C. per μg protein.

Table 2 above shows that: (i) mock-infected Rab(BU) cells, i.e., tk− cells, have negligible TK activity; (ii) TK activity is acquired by Rab(BU) cells after infection with the tk+ BUK-5); but (iii) TK activity is not acquired after infection by the insertion mutant virus, i.e., the clones of PRV(BUK-β-Gal). Thus, like PRV(BUK-dl 3), the clones of PRV(BUK-β-Gal) are tk− PRV.

While the invention has been described in detail and with reference to specific embodiments thereof, it will be apparent to one skilled in the art that various changes and modifications can be made therein without departing from the spirit and scope thereof.

We claim:

1. A pseudorabies virus which fails to produce any functional thymidine kinase as a result of an insertion in the tk gene.

2. The pseudorabies virus as claimed in claim 1, wherein said insertion is about 8 to 5000 bp in size.

3. The pseudorabies virus as claimed in claim 1, wherein said pseudorabies virus also fails to produce any glycoprotein gI as a result of a mutation in the gI gene.

4. The pseudorabies virus as claimed in claim 1, wherein said pseudorabies virus is also temperature-resistant.

5. The pseudorabies. virus as claimed in claim 1, wherein said pseudorabies virus is lyopholized.

6. A pseudorabies virus which fails to produce any functional thymidine kinase as a result of an insertion in the tk gene produced by the process comprising:
   (1) Constructing a hybrid plasmid comprising a cloning vector and a DNA fragment of pseudorabies virus containing substantially all of the pseudorabies virus tk gene and flanking sequence thereof;
   (2) Inserting a foreign DNA sequence within the pseudorabies virus tk gene of the resulting hybrid plasmid of step (1);
   (3) Co-transfecting into pseudorabies virus host cells, the hybrid plasmid of step (2) with infectious DNA from a tk+ pseudorabies virus; and
   (4) Selecting in tk− pseudorabies virus host cells, for tk− pseudorabies virus from the virus produced in step (3) so as to produce a pseudorabies virus mutant which fails to produce any functional thymidine kinase as a result of an insertion in the tk gene.

7. The pseudorabies virus as claimed in claim 6, wherein said insertion is about 8 to 5000 bp in size.

8. The pseudorabies virus as claimed in claim 6, wherein said pseudorabies. virus mutant also fails to produce any gI glycoprotein as a result of a mutation in the gI gene.

9. The pseudorabies virus as claimed in claim 6, wherein the infectious DNA of step (3) is derived from temperature-resistant pseudorabies virus such that the resulting mutants of step (3) are temperature-resistant pseudorabies virus mutants which fail to produce any functional thymidine kinase as a result of an insertion in the tk gene.

10. The pseudorabies virus as claimed in claim 6, additionally comprising step (5):
(5) Propagating the resulting pseudorabies virus of step (4) at a non-permissive temperature for a temperature-sensitive virus so as to select for and produce temperature-resistant pseudorabies virus mutants which fail to produce any functional thymidine kinase as a result of an insertion in the tk gene.

11. The pseudorabies virus as claimed in claim 6, wherein said cloning vector is selected from the group consisting of pBR322, pBR325, pKH47, pBR328, pHC79, phage Charon 28, pKB11, pKSV-10 and pMAR420.

12. The pseudorabies virus as claimed in claim 11, wherein said cloning vector is pBR322.

13. The pseudorabies virus as claimed in claim 6, wherein said pseudorabies virus host cells in step (3) are tk+ pseudorabies virus host cells.

14. The pseudorabies virus as claimed in claim 6, wherein said pseudorabies virus as lyopholized.

* * * * *

UNITED STATES PATENT AND TRADEMARK OFFICE
CERTIFICATE OF CORRECTION

PATENT NO. : 4,999,296

DATED : March 12, 1991

INVENTOR(S) :
MALON KIT, SAUL KIT

It is certified that error appears in the above-indentified patent and that said Letters Patent is hereby corrected as shown below:

In column 1, line 9, after "Human Services.", insert -- The Government has certain rights. --

Signed and Sealed this

Eleventh Day of April, 1995

Attest:

BRUCE LEHMAN

Attesting Officer     Commissioner of Patents and Trademarks